(12) United States Patent
Murakawa et al.

(10) Patent No.: US 10,271,759 B2
(45) Date of Patent: Apr. 30, 2019

(54) BODY FAT MEASUREMENT DEVICE

(71) Applicants: Yasuaki Murakawa, Kyoto (JP);
Takehiro Hamaguchi, Kyoto (JP);
Kazuhisa Tanabe, Kyoto (JP);
Hiromichi Karo, Kyoto (JP)

(72) Inventors: Yasuaki Murakawa, Kyoto (JP);
Takehiro Hamaguchi, Kyoto (JP);
Kazuhisa Tanabe, Kyoto (JP);
Hiromichi Karo, Kyoto (JP)

(73) Assignee: FUKUDA DENSHI CO., LTD., Tokyo (JP)

( * ) Notice: Subject to any disclaimer, the term of this patent is extended or adjusted under 35 U.S.C. 154(b) by 1898 days.

(21) Appl. No.: 13/691,195

(22) Filed: Nov. 30, 2012

(65) Prior Publication Data
US 2013/0090543 A1 Apr. 11, 2013

Related U.S. Application Data

(63) Continuation-in-part of application No. PCT/JP2011/063496, filed on Jun. 13, 2011.

(30) Foreign Application Priority Data

Jul. 15, 2010 (JP) .................................. 2010-160838

(51) Int. Cl.
*A61B 5/00* (2006.01)
*A61B 5/08* (2006.01)
*A61B 5/053* (2006.01)

(52) U.S. Cl.
CPC .......... *A61B 5/0537* (2013.01); *A61B 5/4872* (2013.01); *A61B 5/7214* (2013.01);
(Continued)

(58) Field of Classification Search
CPC ... A61B 5/0537; A61B 5/0809; A61B 5/4869; A61B 5/4872; A61B 5/4875;
(Continued)

(56) References Cited

U.S. PATENT DOCUMENTS 6,766,272 B2 * 7/2004 Serita .................. A61B 5/0537
702/155
7,798,963 B2 * 9/2010 White ................. A61B 5/0402
600/437

(Continued)

FOREIGN PATENT DOCUMENTS

JP   A-2004-135698   5/2004
JP   A-2005-118148   5/2005
(Continued)

OTHER PUBLICATIONS

Jul. 5, 2011 International Search Report issued in International Application No. PCT/JP2011/063496 (with translation).

*Primary Examiner* — Adam J Eiseman
(74) *Attorney, Agent, or Firm* — Oliff PLC

(57) ABSTRACT

A body fat measurement device includes: a measurement unit for measuring a shape of a measurement subject's trunk area; a breathing estimation unit that detects a change over time in the measured trunk area shape and estimates the measurement subject's breathing based on the detected change; a breathing state determination unit that determines whether or not the estimated breathing of the measurement subject is in a state suited to measurement; a state output unit that outputs the estimated breathing state to the exterior in association with a result of the determination; and a fat mass calculation unit that calculates a trunk area fat mass using the body impedance measured by a body impedance measurement unit and a trunk area size based on the trunk area shape measured by the measurement unit.

7 Claims, 18 Drawing Sheets

(52) U.S. Cl.
CPC .......... *A61B 5/7278* (2013.01); *A61B 5/7285* (2013.01); *A61B 5/0809* (2013.01); *A61B 5/6823* (2013.01); *A61B 5/6825* (2013.01); *A61B 5/6829* (2013.01)

(58) Field of Classification Search
CPC ... A61B 5/4878; A61B 5/4881; A61B 5/6823; A61B 5/7285; A61B 5/7289; A61B 5/7292; A61B 5/1075
See application file for complete search history.

(56) References Cited

U.S. PATENT DOCUMENTS

| | | | | |
|---|---|---|---|---|
| 2004/0249264 | A1* | 12/2004 | Salgo | A61B 5/087 600/413 |
| 2006/0235327 | A1* | 10/2006 | Masuo | A61B 5/0537 600/547 |
| 2007/0038140 | A1* | 2/2007 | Masuo | A61B 5/0537 600/547 |
| 2007/0043302 | A1* | 2/2007 | Masuo | A61B 5/0537 600/547 |
| 2007/0244363 | A1* | 10/2007 | Sano | A61B 1/00039 600/158 |
| 2009/0024053 | A1 | 1/2009 | Kasahara | |
| 2009/0093732 | A1* | 4/2009 | Kasahara | A61B 5/0537 600/547 |
| 2010/0121216 | A1* | 5/2010 | Hamaguchi | A61B 5/0537 600/547 |
| 2010/0130885 | A1* | 5/2010 | Hamaguchi | A61B 5/0537 600/547 |
| 2010/0198100 | A1 | 8/2010 | Oku et al. | |

FOREIGN PATENT DOCUMENTS

| | | | | |
|---|---|---|---|---|
| JP | A-2007-268142 | | 10/2007 | |
| JP | WO 2008146663 | A1 * | 12/2008 | ............ A61B 5/0537 |
| JP | A-2009-22482 | | 2/2009 | |
| JP | A-2009-22515 | | 2/2009 | |
| JP | A-2009-160435 | | 7/2009 | |

* cited by examiner

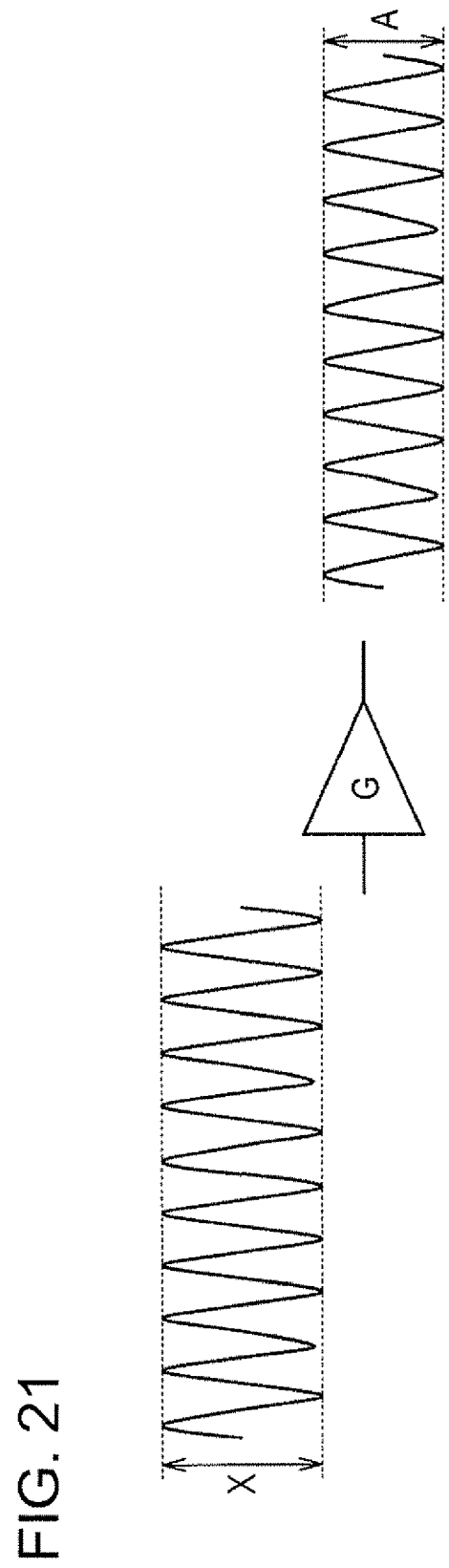

BODY FAT MEASUREMENT DEVICE

This is a Continuation of Application No. PCT/JP2011/063496 filed Jun. 13, 2011, which claims the benefit of Japanese Patent Application No. 2010-160838 filed Jul. 15, 2010. The disclosure of the prior applications is hereby incorporated by reference herein in its entirety.

TECHNICAL FIELD

This invention relates to body fat measurement devices capable of calculating the body fat mass of a measurement subject by measuring a body impedance, and particularly relates to body fat measurement devices capable of easily measuring a body fat mass in a household or the like.

BACKGROUND ART

Thus far, a method that measures a body impedance using electrodes brought into contact with the surface of a body and then calculates a body fat mass using the measured body impedance and a predetermined computation formula has been known as a method for measuring the body fat mass of a person with ease, even in a household.

However, when the measurement subject breathes and his/her trunk area expands/contracts as a result, the positions of his/her internal organs change, and the body impedance value changes as a result. In order to eliminate this influence of breathing, normally, the measurement subject holds his/her breath. However, holding his/her breath places a physical burden on the measurement subject.

Accordingly, JP 2007-268142A (Patent Literature 1), for example, discloses a method that enables the measurement to be carried out without the measurement subject holding his/her breath, or that only requires the measurement subject who hold his/her breath for a short period.

The method disclosed in JP 2007-268142A (Patent Literature 1) measures an impedance multiple times, and when the impedance values measured each time in synchronization with the breathing of the measurement subject in a state where it is determined that the measured impedance value is not erroneous converge, the convergence value is taken as the final value of the impedance for calculating the body fat mass. Meanwhile, although another method disclosed in JP 2007-268142A (Patent Literature 1) requires the measurement subject to hold his/her breath, the method reduces the period for which the breath must be held by issuing a notification prompting the measurement subject to hold his/her breath when the stated convergence has been detected.

CITATION LIST

Patent Literature

Patent Literature 1: JP 2007-268142A

SUMMARY OF INVENTION

Technical Problem

The detection of the convergence of the impedance value according to JP 2007-268142A (Patent Literature 1) is based on the principle that if the measurement subject breathes in a stable manner, the impedance values will converge. However, JP 2007-268142A (Patent Literature 1) does not provide a function for the measurement subject him/herself to confirm whether or not he/she is breathing in a stable manner; it is thus difficult for the measurement subject to bring his/her breathing state to a stable state so that the impedance values can converge, and is therefore lacking in convenience.

Accordingly, it is an object of this invention to provide a body fat measurement device capable of accurately and easily measuring a fat mass.

Solution to Problem

A body fat measurement device according to the present invention includes: multiple electrodes for making contact with the surface of a measurement subject's body at the measurement subject's trunk area; an impedance measurement unit that measures a body impedance of the measurement subject using the multiple electrodes; a measurement unit for measuring a shape of the measurement subject's trunk area; an estimation unit that detects a change over time in the trunk area shape measured by the measurement unit and estimates the measurement subject's breathing based on the detected change; a determination unit that determines whether or not the measurement subject's breathing estimated by the estimation unit is in a state suited to measurement; a state output unit that outputs the breathing state estimated by the estimation unit to the exterior in association with a result of the determination performed by the determination unit; and a fat mass calculation unit that calculates a trunk area fat mass using the body impedance measured by the impedance measurement unit and a trunk area size based on the trunk area shape measured by the measurement unit; and a control unit that controls the impedance measurement unit and the fat mass calculation unit.

The state suited to measurement indicates a stopped state in which the measurement subject has stopped breathing after exhaling. The measurement unit is includes a dimension measurement unit for measuring a dimension of the measurement subject's trunk area, and the trunk area shape is detected based on the dimension of the trunk area measured by the dimension measurement unit. The determination unit includes a breathing determination unit that determines whether the measurement subject is breathing or is in the stopped state based on a result of comparing an amount of change in the dimension of the trunk area measured by the dimension measurement unit with an amount of change in the dimension of the trunk area during the stopped state that has been detected in advance. The control unit causes the body impedance measurement to be started by the impedance measurement unit when the breathing determination unit has determined that the breathing of the measurement subject is in the stopped state.

Advantageous Effects of Invention

According to the present invention, when measuring a fat mass, the breathing state of a measurement subject is outputted in association with a result of a determination as to whether or not the breathing is in a state suited to measurement. Through this, the measurement subject can easily transit his/her breathing state to a state suited to measurement, which makes it possible to easily and accurately carry out the measurement.

BRIEF DESCRIPTION OF DRAWINGS

FIG. 21 is a diagram illustrating a threshold determination process according to the embodiment of the present invention.

DESCRIPTION OF EMBODIMENTS

Figure 1A:
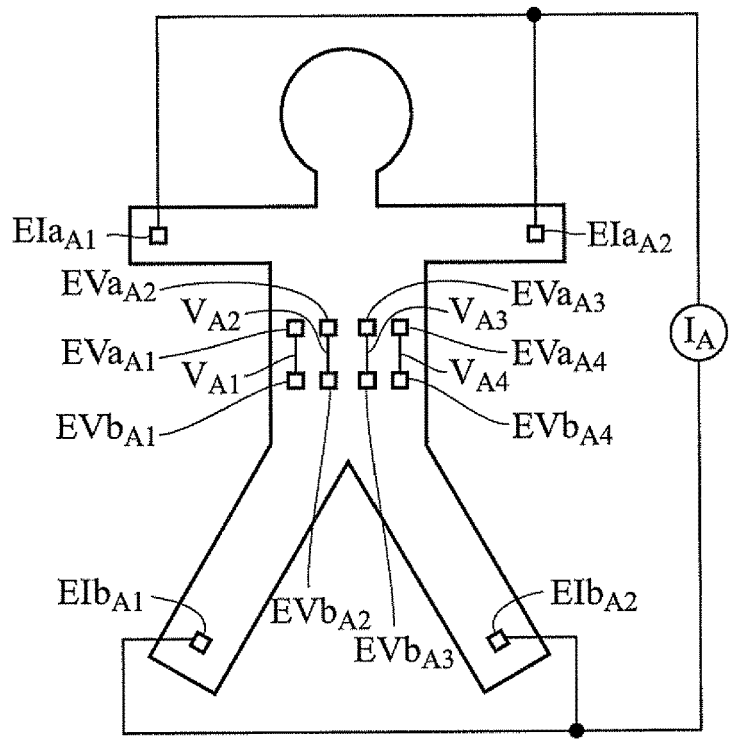
FIGS. 1A and 1B are diagrams illustrating the fundamentals of measurement performed by a body fat measurement device according to an embodiment of the present invention.

Hereinafter, an embodiment of the present invention will be described in detail with reference to the drawings. Note that in the following embodiment, identical or corresponding elements are given the same reference numerals in the drawings, and descriptions thereof will not be repeated.

First, terms expressing the parts of the human body will be defined. "Trunk area" as mentioned in the present embodiment refers to the area excluding the head, neck, and four limbs, and corresponds to what is known as the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. "Body axis" refers to an axis located along the direction in which the trunk area extends, or in other words, an axis that passes through the approximate center of a side cross-section of the measurement subject's trunk area and that extends in a direction approximately perpendicular to the stated side cross-section.

The "depth" of the trunk area indicates the diametric length orthogonal to the body axis and passing through the navel in a side cross-section of the area of the trunk area that corresponds to the location of the navel, whereas the "width" of the trunk area indicates the diametric length orthogonal to the body axis and orthogonal to the diameter of the "depth" of the trunk area in a side cross-section of the area of the trunk area that corresponds to the location of the navel.

Finally, in the present embodiment, "breathing" refers to abdominal breathing that primarily involves movement of the diaphragm. "Stable breathing state" refers to a state in which breathing without excessive inhalation and exhalation is repeated over a constant cycle.

Fundamentals of Body Fat Measurement

Figure 1B:
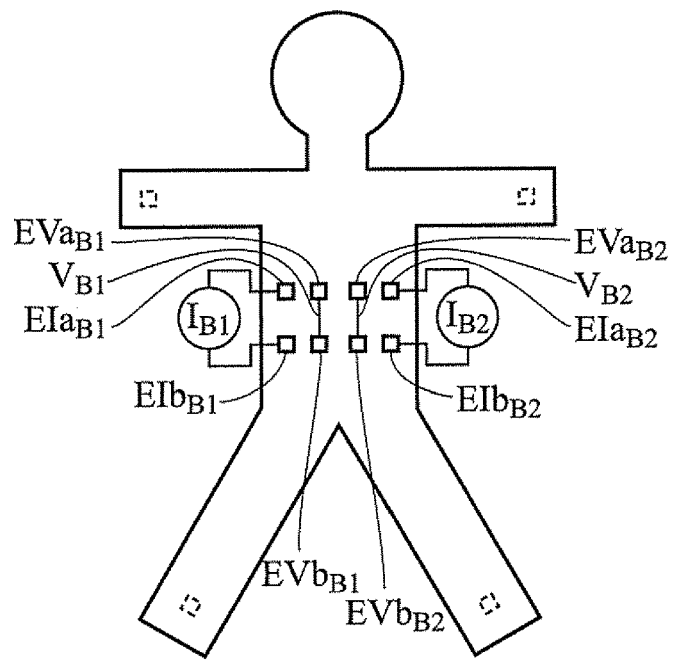

FIGS. 1A and 1B are diagrams illustrating the fundamentals of measurement performed by a body fat measurement device according to an embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 1A and 1B. Note that FIGS. 1A and 1B both illustrate the measurement subject from the back side thereof.

As shown in FIG. 1A, electrodes $EIa_{A1}$ and $EIa_{A2}$ are attached to the surface of the left hand of the measurement subject and the surface of the right hand of the measurement subject, respectively, in order to obtain the body impedance for the entire trunk area. Likewise, electrodes $EIb_{A1}$ and $EIb_{A2}$ are attached to the surface of the left foot of the measurement subject and the surface of the right foot of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIb_{A1}$, and $EIb_{A2}$ attached to both hands and both feet, respectively. While the constant current $I_A$ is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current $I_A$ is flowing between both hands and both feet, which are positioned at a distance from the trunk area, and thus almost all of the applied constant current $I_A$ passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current $I_A$ is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{B1}$ and $EIb_{B1}$, and a constant current $I_{B2}$ that passes through the back area locally is applied to the measurement subject using the pair of electrodes $EIa_{B2}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be calculated in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass, Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2a and the depth of the trunk area is taken as 2b, and because the trunk area has a generally oval cross-sectional shape, the trunk area cross-sectional area St can be approximated through the following Formula (2).

$$St = \pi \times a \times b \qquad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient $\alpha$ for reducing error. This coefficient $\alpha$ is obtained, for example, by finding the optimum value for $\alpha$ that fulfills $St' = \alpha \times \pi \times a \times b$, from the relationship between the stated a and b and a trunk area cross-sectional area St' obtained from a sample of a large number of X-ray CT (computed tomography) images.

Accordingly, the stated Formula (2) can approximate with a lower degree of error through the following Formula (3) by using the coefficient $\alpha$.

$$St = \alpha \times \pi \times a \times b \qquad \text{Formula (3)}$$

Note that it is preferable to optimize the coefficient $\alpha$ multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient $\alpha$ in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa=\beta \times a \times (1/Zt) \qquad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, the stated coefficient $\beta$ is a coefficient for converting the body impedance Zt of the entire trunk area into the non-fat cross-sectional area Sa, and an optimum value can be found, for example, based on a sample of a large number of X-ray CT images, in the same manner as when finding the coefficient $\alpha$. In other words, the optimum value for the coefficient $\beta$ that fulfils Sa'=$\beta \times a \times (1/Zt)$ can be found from the relationship between a non-fat cross-sectional area Sa' obtained from a sample of a large number of X-ray CT images, the body impedance Zt of the entire measurement subject's trunk area imaged by the X-ray CT, and the stated a.

Note that it is preferable for the stated coefficient $\beta$ to be optimized as appropriate in accordance with the measurement subject information, in the same manner as the coefficient $\alpha$ mentioned above. In other words, the non-fat cross-sectional area Sa can be approximated with a higher degree of accuracy by changing the value of the stated coefficient $\beta$ in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb=\gamma \times a \times Zs \qquad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, the stated coefficient $\gamma$ is a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient $\alpha$ or the coefficient $\beta$. In other words, the optimum value for the coefficient $\gamma$ that fulfils Sb'=$\gamma \times a \times Zs$ can be found from the relationship between a subcutaneous fat cross-sectional area Sb' obtained from a sample of a large number of X-ray CT images, the body impedance Zs of the surface layer area on the back area side of the measurement subject's trunk area imaged by the X-ray CT, and the stated a.

Note that it is preferable for the stated coefficient $\gamma$ to be optimized as appropriate in accordance with the measurement subject information, in the same manner as the coefficient $\alpha$ and the coefficient $\beta$ mentioned above. In other words, the subcutaneous fat cross-sectional area Sb can be approximated with a higher degree of accuracy by changing the value of the stated coefficient $\gamma$ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx=\alpha \times \pi \times a \times b - \beta \times a \times (1/Zt) - \gamma \times a \times Zs \qquad \text{Formula (6)}$$

Note that the coefficients $\alpha$, $\beta$, and $\gamma$ are assumed to be included in a coefficient group 293, which will be mentioned later.

Functional Configuration

The functional configuration of the body fat measurement device according to the present embodiment will now be described with reference to FIG. 2.

Figure 2:
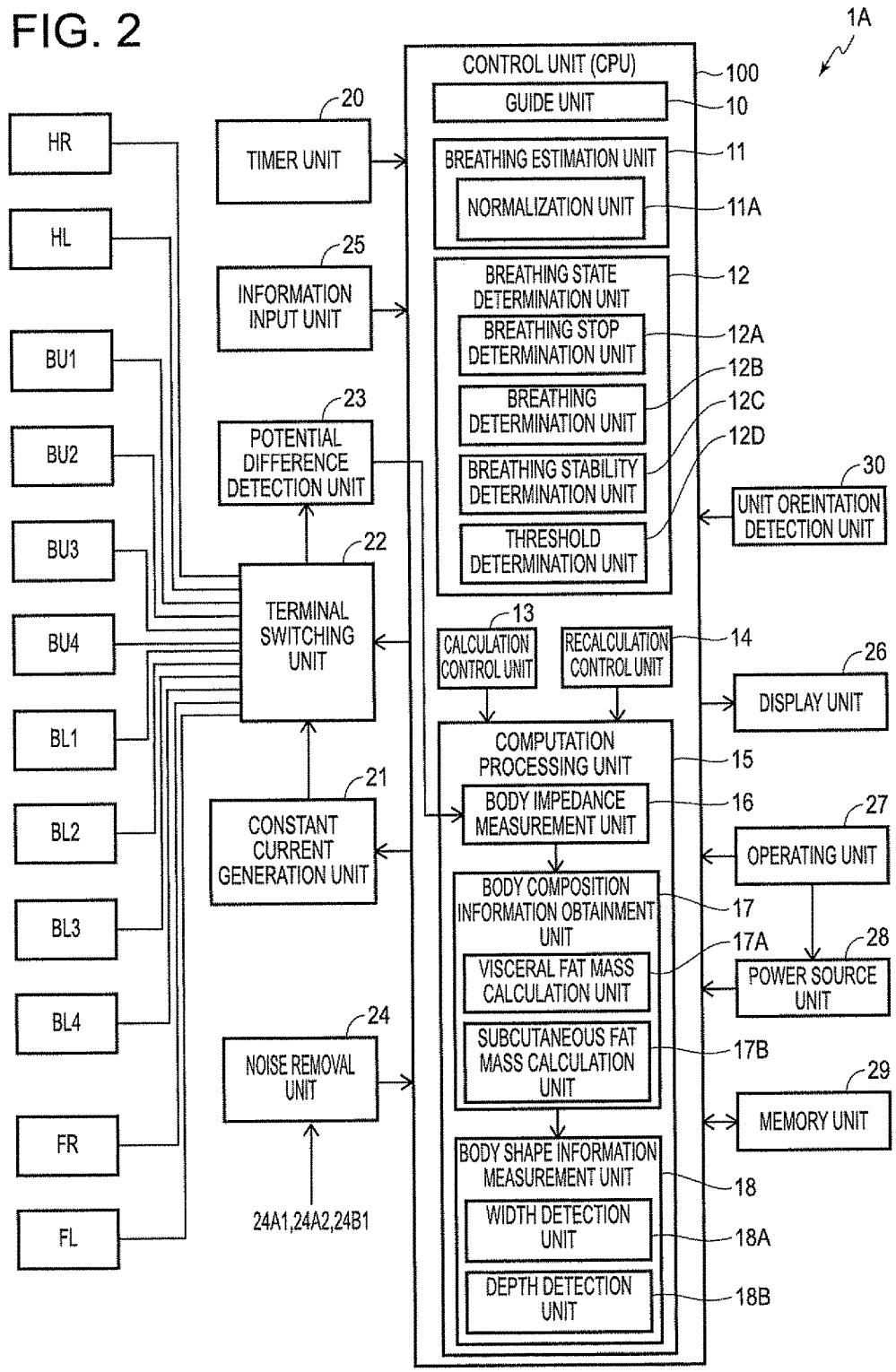
FIG. 2 is a diagram illustrating the functional configuration of the body fat measurement device according to the embodiment.

As shown in FIG. 2, a body fat measurement device 1A includes: a control unit 100; a timer unit 20; a constant current generation unit 21; a terminal switching unit 22; a potential difference detection unit 23; a noise removal unit 24 that is linked to optical sensors, mentioned later, for measuring dimensions of the trunk area; an information input unit 25; a display unit 26; an operating unit 27; a power source unit 28; a memory unit 29; a unit orientation detection unit 30; and multiple electrodes for making contact with the surface of the measurement subject's body. The multiple electrodes include electrodes HR, HL, BU1-BU4, BL1-BL4, FR, and FL.

The control unit 100 is configured of a microprocessor including a CPU (central processing unit). The control unit 100 includes a guide unit 10 that provides guidance information and the like for measurement to the measurement subject, a breathing estimation unit 11, a breathing state determination unit 12, a calculation control unit 13, a recalculation control unit 14, and a computation processing unit 15. The functions of the respective units within the control unit 100 are realized by programs or by combinations of programs and circuitry. The programs are stored in advance in the memory unit 29, and the functions thereof are realized by the CPU reading out the programs from the memory unit 29 and executing those programs. The guide unit 10 is described here as outputting the guidance information using a display, but the information may be outputted through audio.

The breathing estimation unit 11 detects changes over time in the measurement subject's trunk area, and estimates the breathing state of the measurement subject based on the detected changes. The calculation control unit 13 and the recalculation control unit 14 control the calculation of the body impedance or the calculation of the fat mass.

In order to estimate the breathing state, the breathing estimation unit 11 includes a normalizing unit 11A for normalizing the amplitude of a voltage signal that has been outputted from the optical sensor and that has passed through the noise removal unit 24. The normalization process carried out by the normalizing unit 11A will be described later.

The breathing state determination unit 12 includes: a breathing stop determination unit 12A for determining that the measurement subject has stopped breathing; a breathing determination unit 12B for determining that the measurement subject is breathing; a breathing stability determination unit 12C for determining a stable breathing state; and a threshold determination unit 12D that determines various types of thresholds referred to for the determinations carried out by these various units.

The computation processing unit 15 includes a body impedance measurement unit 16, a body composition information obtainment unit 17, and a body shape information measurement unit 18 that has trunk area width and depth detection units 18A and 18B. The body composition information obtainment unit 17 includes a visceral fat mass calculation unit 17A and a subcutaneous fat mass calculation unit 17B.

The aforementioned multiple electrodes include: hand electrodes HR and HL serving as upper limb electrodes placed in contact with surfaces of the upper limbs of the measurement subject; back area electrodes BU1-BU4 and BL1-BL4 placed in contact with the back area surface of the measurement subject; and foot electrodes FR and FL serving as lower limb electrodes placed in contact with surfaces of the lower limbs of the measurement subject. Of these, the hand electrodes HR and HL are placed in contact with the measurement subject's palms, whereas the foot electrodes FR and FL are placed in contact with the soles of the measurement subject's feet. Meanwhile, as shown in FIGS. 1A and 1B, the back area electrodes BU1-BU4 and BL1-BL4 are arranged in rows and placed in contact with the back area surface of the measurement subject. Note that the hand electrodes HR and HL, back area electrodes BU1-BU4 and BL1-BL4, and foot electrodes FR and FL are all electrically connected to the aforementioned terminal switching unit 22.

The terminal switching unit 22 is configured of, for example, a relay circuit; based on instructions inputted from the control unit 100, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 100, the respective multiple electrodes HR, HL, BU1-BU4, BL1-BL4, FR, and FL function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction provided by the control unit 100, and supplies the generated constant current to the stated constant current application electrodes via the terminal switching unit 22. A high-frequency current (for example, 50 kHz, 500 µA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 100. Through this, the potential difference between the potential difference detection electrodes is detected in a state in which the aforementioned constant current is applied to the measurement subject.

The trunk area width detection unit 18A is a detection unit for measuring the width of the measurement subjects trunk area without making contact therewith, and detects the width based on a signal outputted from a range sensor such as an optical sensor. The trunk area depth detection unit 18B is a detection unit for measuring the depth of the measurement subject's trunk area without making contact therewith, and detects the depth based on a signal outputted from a range sensor such as an optical sensor. By using non-contact range sensors in this manner, the width and depth can be measured without placing a burden on the body.

The information input unit 25 is a unit for obtaining information regarding the measurement subject used in computation processes carried out by the computation processing unit 15, and is configured of, for example, keys and the like that can be depressed by the measurement subject. Here, the measurement subject information includes at least one of the sex, age, height, weight, and so on of the measurement subject, as mentioned above. The information input unit 25 accepts the input of the measurement subject information, and outputs the accepted measurement subject information to the control unit 100. Note that the information input unit 25 is not absolutely necessary in the configuration of the present invention, and whether or not to provide the information input unit 25 can be determined based on whether or not it is necessary to use the measurement subject information in the computation processes performed by the computation processing unit 15.

The unit orientation detection unit 30 is a detection unit for detecting the orientation of a fitting unit 100A (mentioned later; see FIGS. 3 through 10), and is configured of, for example, an accelerometer. The unit orientation detection unit 30 outputs a signal based on a detection value to the control unit 100.

The body impedance measurement unit 16 calculates the body impedance based on a signal inputted from the potential difference detection unit 23, and outputs that body impedance to the body composition information obtainment unit 17. The body shape information measurement unit 18 outputs, to the body composition information obtainment unit 17, the width and depth of the measurement subject's trunk area calculated by the width detection unit 18A and the depth detection unit 18B. The body composition information obtainment unit 17 includes the visceral fat mass calculation unit 17A and the subcutaneous fat mass calculation unit 17B. The body composition information obtainment unit 17 calculates and obtains the body composition information based on the body impedance inputted from the body impedance measurement unit 16, the width and depth of the trunk area inputted from the body shape information measurement unit 18, and in some cases, the measurement subject information inputted from the information input unit 25 as well. More specifically, the visceral fat mass calculation unit 17A calculates a visceral fat mass and the subcutaneous fat mass calculation unit 17B calculates a subcutaneous fat mass.

The display unit 26 is configured of, for example, an LCD (liquid-crystal display) or the like, and displays the body composition information calculated by the body composition information obtainment unit 17 as mentioned above. More specifically, the visceral fat mass calculated by the visceral fat mass calculation unit 17A and the subcutaneous fat mass calculated by the subcutaneous fat mass calculation unit 17B are displayed in the display unit 26 based on signals outputted from the control unit 100. Here, with the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The display unit 26 also has a function for displaying the orientation of the fitting unit 100A detected by the stated unit orientation detection unit 30. More specifically, based on a signal outputted from the control unit 100, the display unit 26 visualizes and displays the orientation of the fitting unit 100A detected by the stated unit orientation detection unit 30. In addition, various types of guidance information regarding breathing, for taking a measurement, are displayed based on a result of the determination performed by the breathing state determination unit 12.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a button that instructs measurement to start, and so on.

The power source unit 28 is a unit for supplying electrical power to the control unit 100, and uses an internal power source such as a battery, an external power source such as an AC outlet, or the like.

The memory unit 29 is configured of any of various types of memories such as a random access memory (RAM), a read-only memory (ROM), or a non-volatile memory, and is a unit for storing various types of data, programs, and the like for the body fat measurement device 1A.

External Appearance of Device

Figure 3:
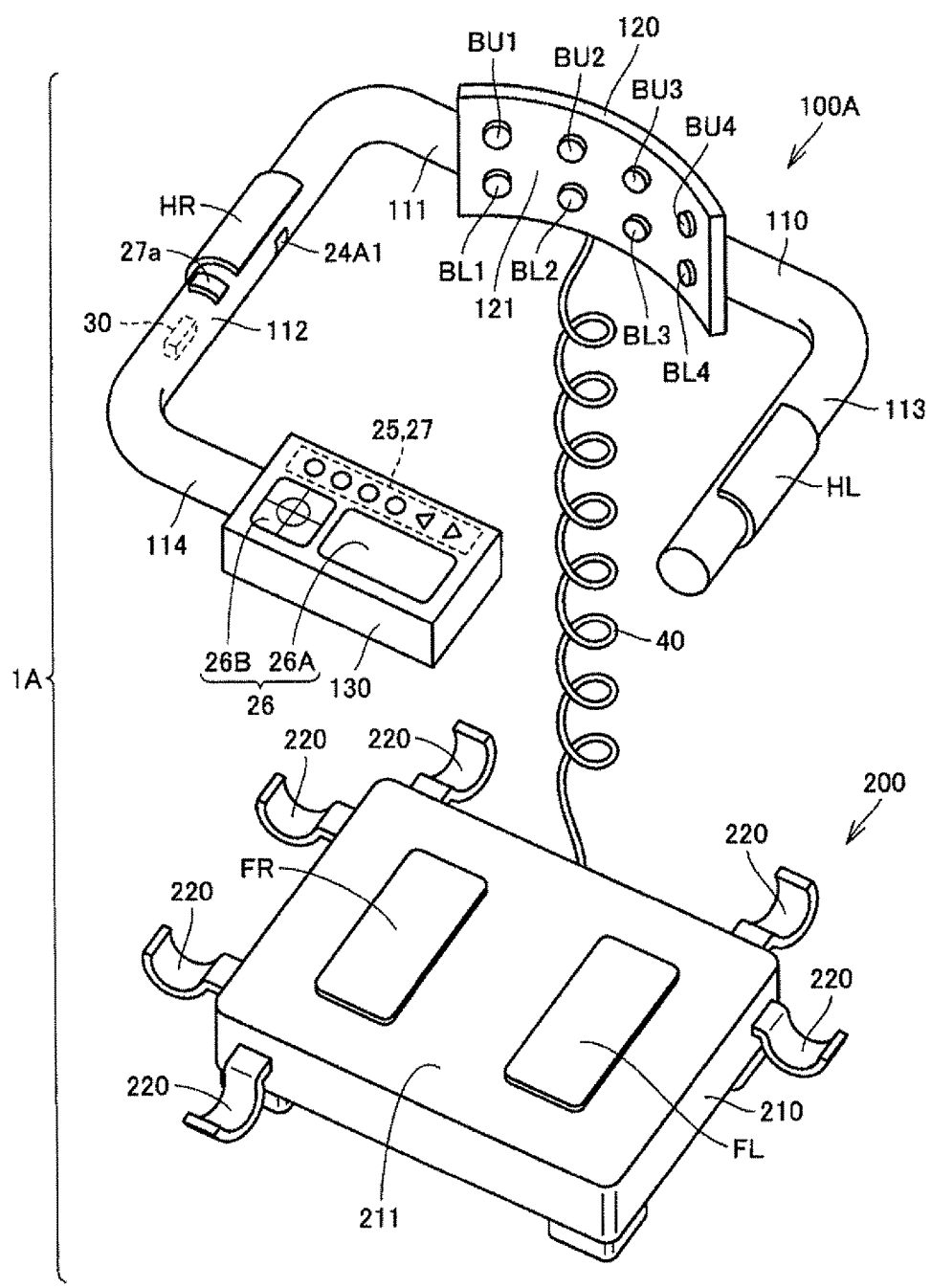
FIG. 3 is a perspective view illustrating the body fat measurement device according to the embodiment of the present invention in an unstored state.
Figure 4:
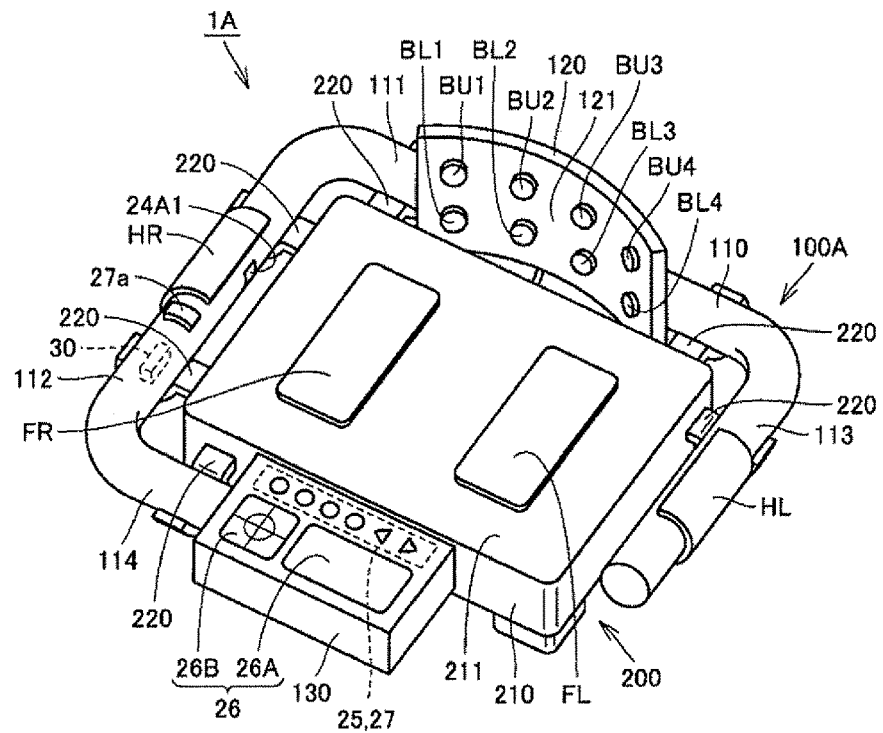
FIG. 4 is a perspective view illustrating the body fat measurement device according to the embodiment of the present invention in a stored state.
Figure 5:
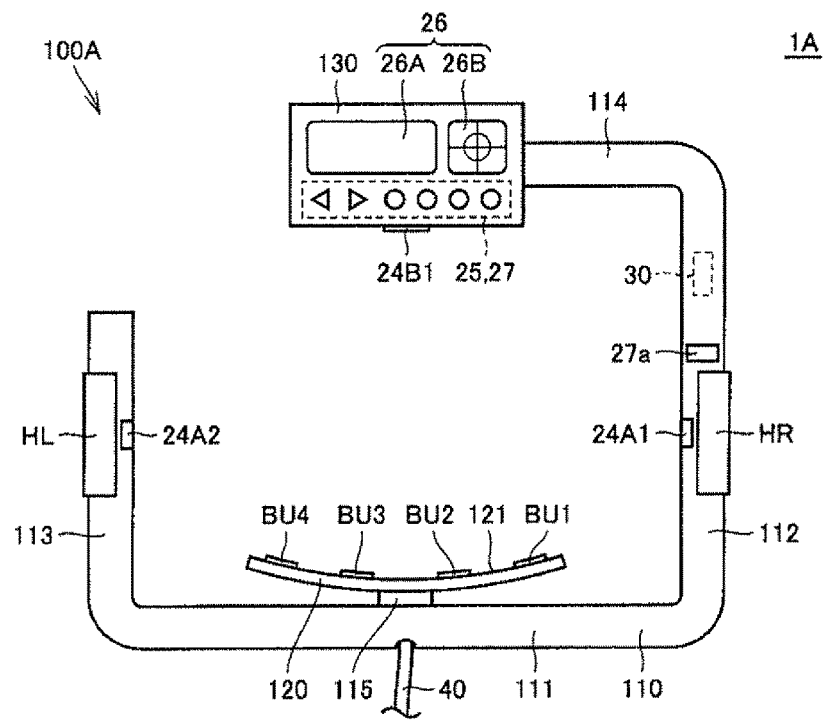
FIG. 5 is a top view of a fitting unit of the body fat measurement device according to the embodiment of the present invention.

FIG. 3 is a perspective view illustrating the body fat measurement device 1A according to the present embodiment in an unstored state, whereas FIG. 4 is a perspective view illustrating a stored state. FIG. 5, meanwhile, is a top view of a fitting unit shown in FIGS. 3 and 4. Next, the structure of the body fat measurement device 1A according to the present embodiment will be described in detail with reference to FIGS. 3 through 5.

As shown in FIGS. 3 and 4, the body fat measurement device 1A according to the present embodiment includes the fitting unit 100A and a platform unit 200. The fitting unit 100A has a frame shape capable of being disposed so as to surround the measurement subject's trunk area in a fitted state, which will be described later. Meanwhile, the platform unit 200 is shaped as a platform onto which the measurement subject can step. Note that the fitting unit 100A and the platform unit 200 are connected by a connection cable 40 that electrically connects electric circuitry provided therein.

As shown in FIGS. 3 through 5, the fitting unit 100A includes: a frame member 110 that includes a rod-shaped rear frame portion 111, a rod-shaped right-side frame portion 112, a rod-shaped left-side frame portion 113, and a rod-shaped front frame portion 114; an electrode support member 120 attached to the rear frame portion 111 of the frame member 110; and a display unit portion 130 attached to the front frame portion 114 of the frame member 110.

The frame member 110 has a frame-shaped outer shape that is approximately rectangular when viewed from above, and has a hollow opening area into which the measurement subject can enter (in other words, into which the measurement subject can insert his/her trunk area). The hollow opening area is defined by the stated rear frame portion 111, right-side frame portion 112, left-side frame portion 113, and front frame portion 114. Note that the left-side frame portion 113 and the front frame portion 114 are not connected, and the aforementioned display unit portion 130 is attached to the end of the front frame portion 114 that is adjacent to the unconnected area.

The electrode support member 120 is disposed in approximately the center of the rear frame portion 111 of the frame member 110 so as to protrude inward. The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120, and preferably, the back area electrodes BU1-BU4 and BL1-BL4 protrude slightly from the front surface 121 of the electrode support member 120. Here, the electrode support member 120 is positioned and attached on the front surface of the rear frame portion 111 so that surfaces of the back area electrodes BU1-BU4 and BL1-BL4 that make contact with the back area surface of the measurement subject face forward during the fitted state, which will be mentioned later.

Meanwhile, as shown in FIG. 5, the electrode support member 120 is attached to the rear frame portion 111 of the frame member 110 via a connection portion 115 including, for example, a ball joint. Through this, the electrode support member 120 is supported by the rear frame portion 111 so as to be capable of swinging. Note that it is preferable for the direction of the swinging to be limited so that the electrode support member 120 can swing only to the left and right in the horizontal plane. Employing such a configuration makes it possible to bring the back area electrodes BU1-BU4 and BL1-BL4 provided on the front surface 121 of the electrode support member 120 into contact with the back area of the measurement subject with certainty and with an appropriate pressure during the fitted state, which will be mentioned later.

Alternatively, the connection portion 115 may be provided with an elastic member such as a spring, and configured so that the electrode support member 120 is elastically supported on the rear frame portion 111. Employing such a configuration makes it possible to bring the back area electrodes BU1-BU4 and BL1-BL4 provided on the front surface 121 of the electrode support member 120 into contact with the back area of the measurement subject with more certainty and with a more appropriate pressure during the fitted state, which will be mentioned later.

As shown in FIGS. 3 through 5, the aforementioned hand electrode HR is provided in approximately the center of the right-side frame portion 112 of the frame member 110. The hand electrode HR is positioned so as to be exposed on the surface of the right-side frame portion 112 of the frame member 110. Meanwhile, the area of the right-side frame portion 112 of the frame member 110 in which the hand electrode HR is provided is formed in a rod shape, so as to be capable of being gripped by the measurement subject's right hand. Here, it is preferable for the surface of the hand electrode HR that makes contact with the palm of the measurement subject's right hand to be disposed so as to mainly face outward from the frame member 110.

An optical sensor 24A1 that corresponds to the stated trunk area width detection unit 18A is embedded within what is approximately the center of the right-side frame portion 112 of the frame member 110. Light emitted from the optical sensor 24A1 is outputted to the exterior via a transmission window (not shown) configured of a transmissive member.

In addition, an accelerometer serving as the aforementioned unit orientation detection unit 30 is embedded within an area near the front end of the right-side frame portion 112 of the frame member 110. The accelerometer is positioned relative to the frame member 110 so as to be capable of detecting whether a plane including an axis line of the frame member 110 (in other words, a plane orthogonal to an axis line of the hollow opening area defined by the frame member 110) is parallel to a horizontal plane, or to what degree the plane is angled relative to the horizontal plane; the configuration is such that multiple accelerometers are combined, if necessary.

Furthermore, a measure button 27a that instructs the start of measurement is provided in a predetermined location of the right-side frame portion 112 of the frame member 110. Preferably, the measure button 27a is provided in a location adjacent to the hand electrode HR. As a result, it is not necessary for the measurement subject to move his/her right hand during measurement, which makes it possible to provide superior operability.

The aforementioned hand electrode HL is provided in approximately the center of the left-side frame portion 113 of the frame member 110. The hand electrode HL is positioned so as to be exposed on the surface of the left-side frame portion 113 of the frame member 110. Meanwhile, the area of the left-side frame portion 113 of the frame member 110 in which the hand electrode HL is provided is formed in a rod shape, so as to be capable of being gripped by the measurement subject's left hand. Here, it is preferable for the surface of the hand electrode HL that makes contact with the palm of the measurement subject's left hand to be disposed so as to mainly face outward from the frame member 110.

An optical sensor 24A2 is embedded within what is approximately the center of the left-side frame portion 113 of the frame member 110, as shown in FIG. 5. Light emitted from the optical sensor 24A2 is outputted to the exterior via a window (not shown) configured of a light-transmissive member.

As shown in FIGS. 3 through 5, the aforementioned display unit portion 130 is attached to the front frame portion 114 of the frame member 110. The display unit 26 is provided in the top surface of the display unit portion 130. Here, the display unit 26 includes a display unit 26A for displaying measurement results, various types of guides, and so on as numbers, text, or graphs, and a display unit 26B for visualizing and displaying the orientation of the fitting unit 100A. Meanwhile, the information input unit 25 and the operating unit 27, excluding the measure button 27a, are provided on an area of the top surface of the display unit portion 130 that is adjacent to the display unit 26. Note that it is preferable for the display unit portion 130 to be located in front of the measurement subject during the fitted state, and for this reason, the display unit portion 130 is disposed forward from the aforementioned electrode support member 120 (that is, in approximately the center of the frame member 110 in the horizontal direction thereof).

Furthermore, an optical sensor 24B1 that corresponds to the depth detection unit 18A is embedded within the display unit portion 130, as shown in FIG. 5. A window (not shown), configured of a member that allows light emitted from the optical sensor 24B1 to pass therethrough, is provided in a rear surface area of the display unit portion 130 in the area thereof in which the optical sensor 24B1 is embedded.

Meanwhile, as shown in FIGS. 3 and 4, the platform unit 200 includes a box-shaped platform portion 210, and support portions 220 that protrude outward from predetermined locations on the front surface, the rear surface, the right-side surface, and the left-side surface of the platform portion 210.

The platform portion 210 has a top surface 211 onto which the measurement subject steps, and the aforementioned foot electrodes FR and FL are respectively provided in predetermined locations of the top surface 211. The foot electrodes FR and FL are positioned so as to be exposed on the top surface of the platform portion 210. Here, the configuration is such that the contact surfaces of the foot electrodes FR and FL that make contact with the sole of the measurement subject's right foot and the sole of the measurement subject's left foot are both facing upward.

As shown in FIG. 4, the support portions 220 are units for supporting and storing the fitting unit 100A during the stored state, and have shapes that are capable of accepting and supporting the rear frame portion 111, the right-side frame portion 112, the left-side frame portion 113, and the front frame portion 114, respectively, of the frame member 110. As shown in FIG. 4, during the stored state, the frame member 110 of the fitting unit 100A is placed so as to surround the platform portion 210 of the platform unit 200. Note that in the stored state, it is preferable for the configuration to be such that the connection cable 40 that connects the fitting unit 100A to the platform unit 200 is contained within the platform unit 200. To achieve such a configuration, a reel member capable of taking up the connection cable 40 into the interior of the platform unit 200 may be provided.

The aforementioned control unit 100, constant current generation unit 21, terminal switching unit 22, potential difference detection unit 23, memory unit 29, and so on shown in FIG. 2 may be provided within the fitting unit 100A, or may be provided within the platform portion 210. Furthermore, although the information input unit 25, the display unit 26, and operating unit 27 are provided in the fitting unit 100A of the body fat measurement device 1A according to the present embodiment, those units may be provided within the platform unit 200.

Fitting Procedure

Figure 6:
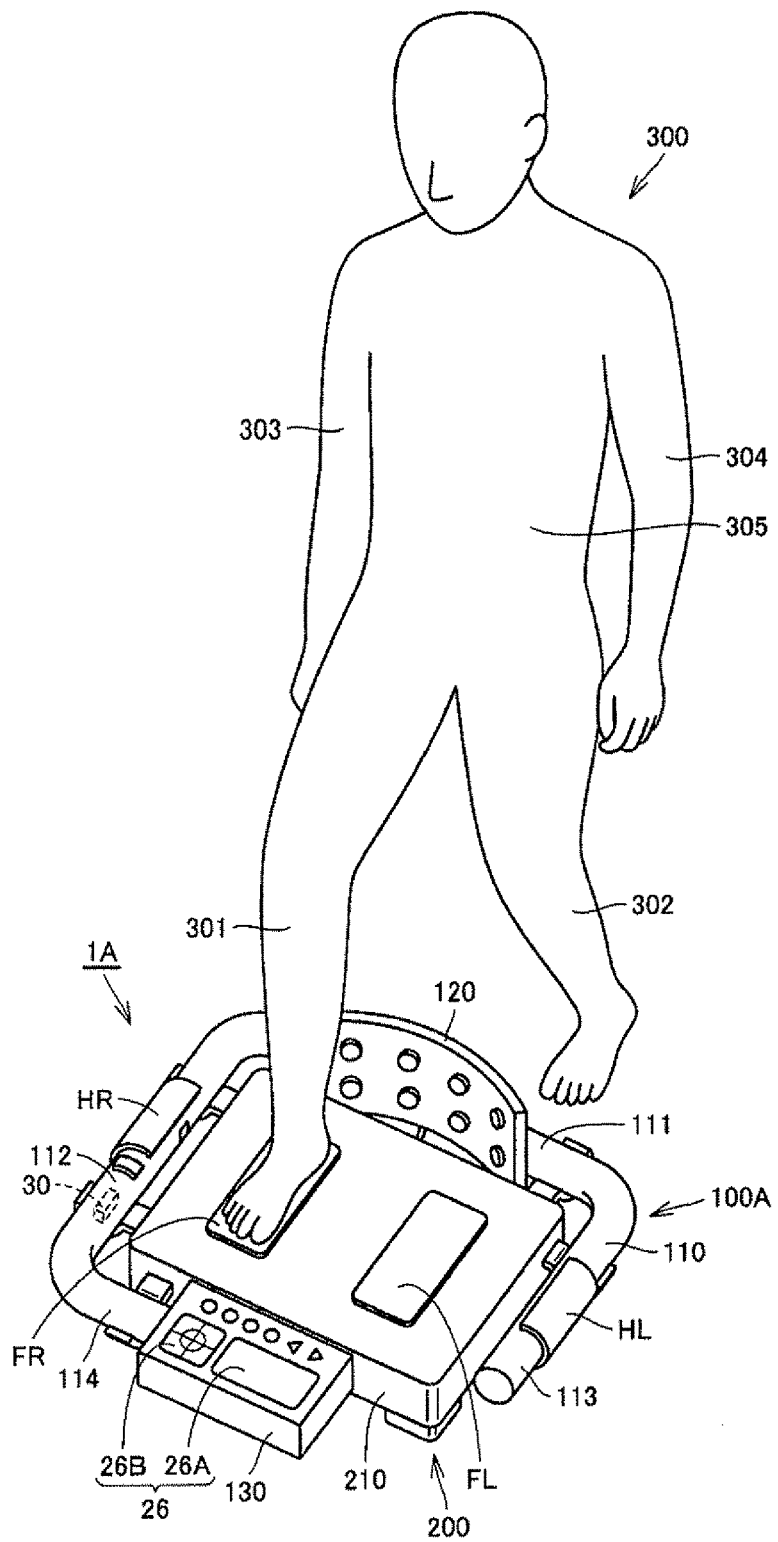
FIG. 6 is a diagram illustrating a procedure to be performed by a measurement subject when carrying out a measurement using the body fat measurement device according to the embodiment of the present invention.
Figure 7:
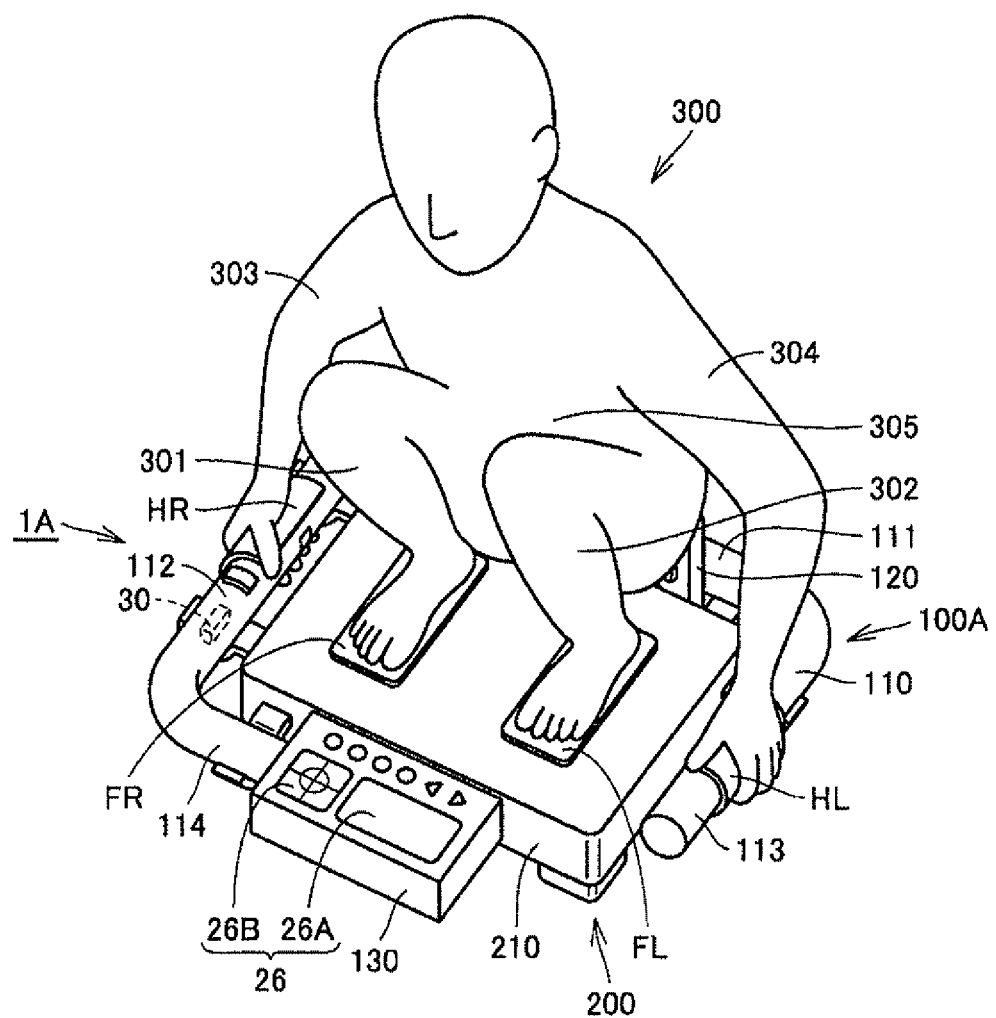
FIG. 7 is a diagram illustrating a procedure to be performed by a measurement subject when carrying out a measurement using the body fat measurement device according to the embodiment of the present invention.
Figure 8:
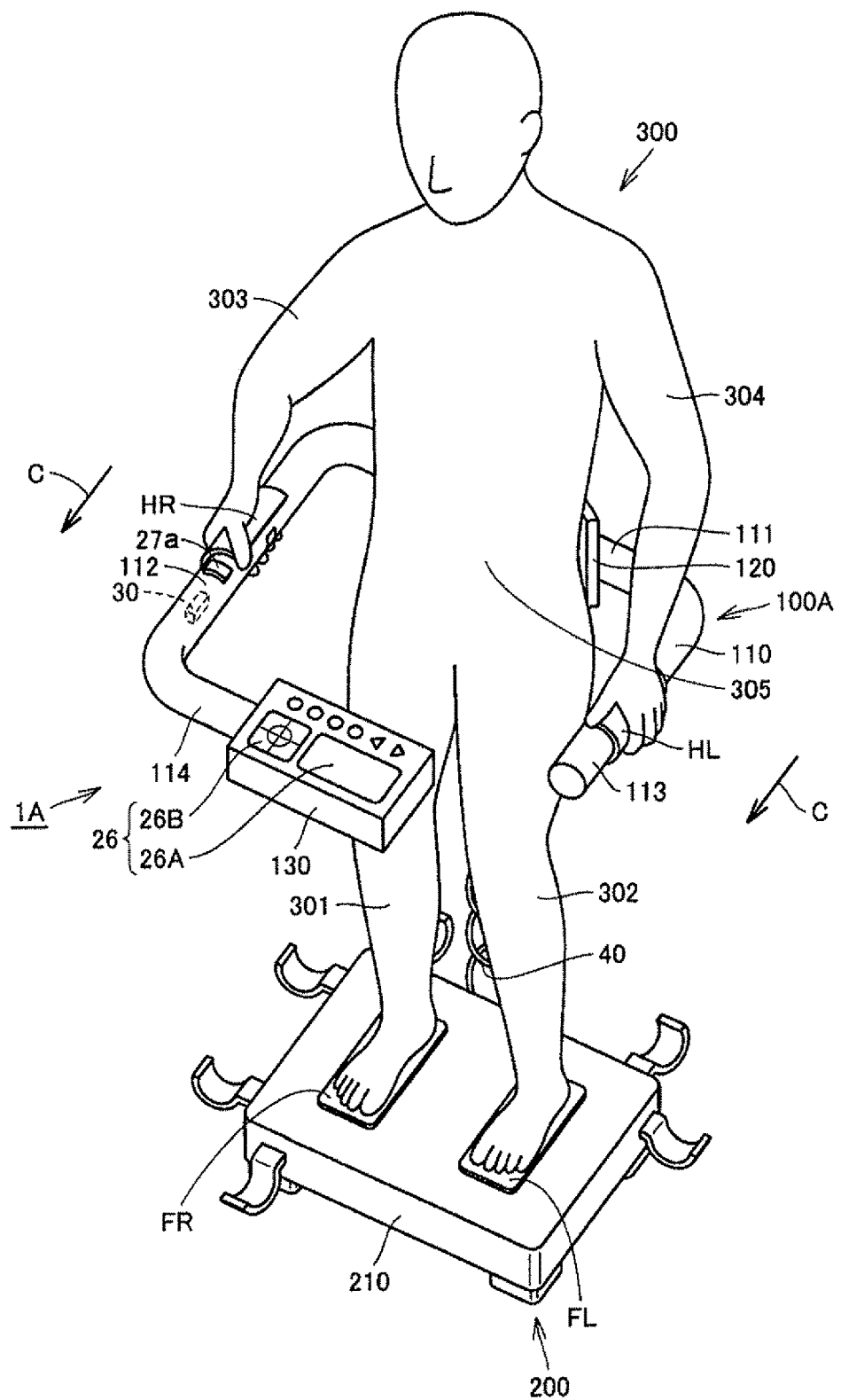
FIG. 8 is a diagram illustrating a procedure to be performed by a measurement subject when carrying out a measurement using the body fat measurement device according to the embodiment of the present invention.
Figure 9:
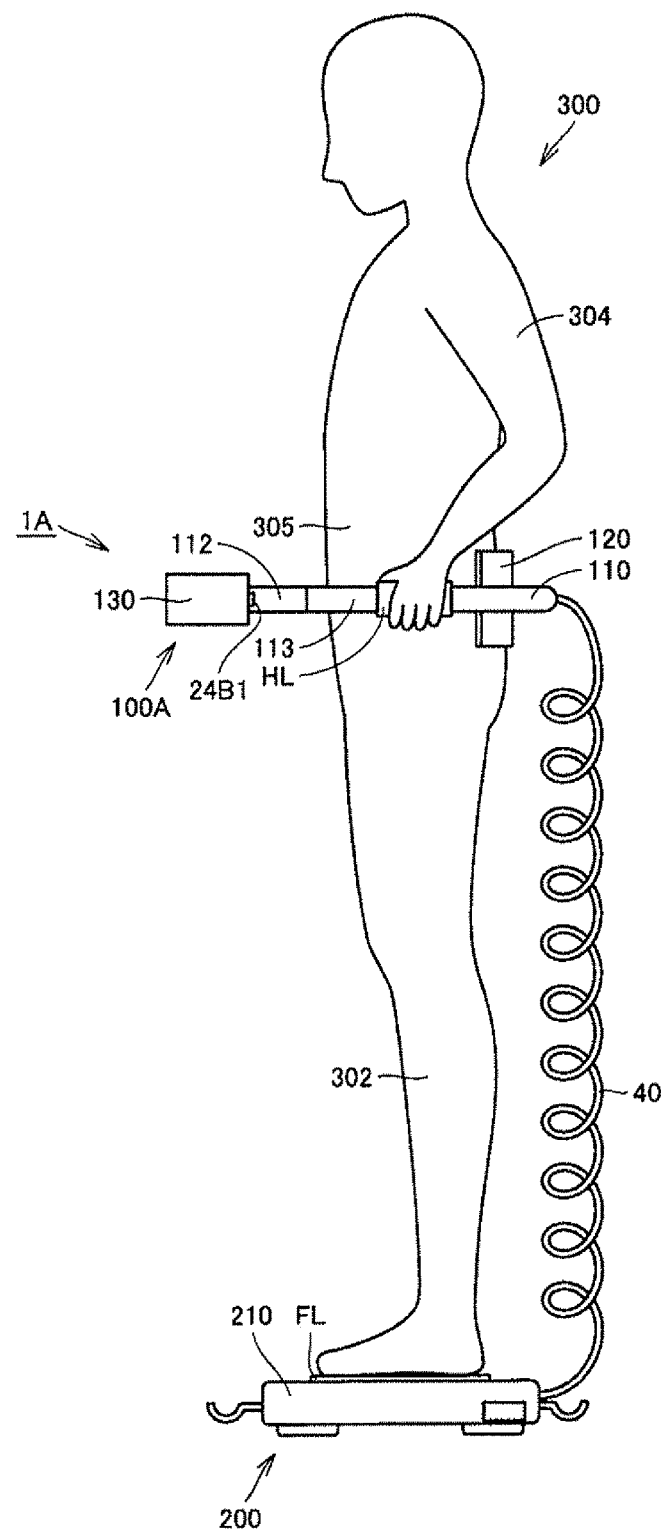
FIG. 9 is a diagram illustrating a fitted state of the fitting unit of the body fat measurement device according to the embodiment of the present invention.
Figure 10:
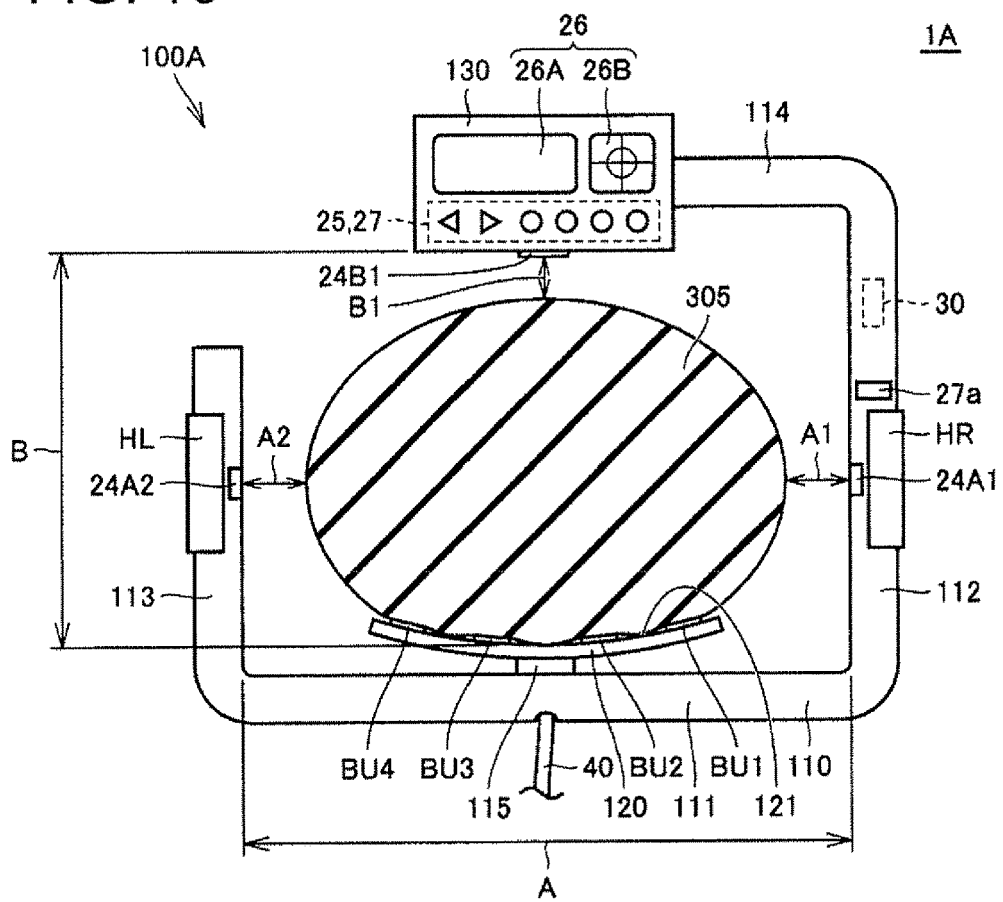
FIG. 10 is a diagram illustrating a distance measurement performed when fitting the fitting unit of the body fat measurement device according to the embodiment of the present invention.

FIGS. 6 through 8 are diagrams illustrating a procedure to be performed by the measurement subject when carrying out a measurement using the body fat measurement device 1A according to the present embodiment. Meanwhile, FIGS. 9 and 10 are diagrams illustrating the fitting unit of the body fat measurement device 1A according to the present embodiment in the fitted state. Next, a procedure to be performed by the measurement subject and the fitted state of the fitting unit when carrying out measurement using the body fat measurement device according to the present embodiment will be described with reference to FIGS. 6 through 10.

As shown in FIG. 6, when measuring body fat mass using the body fat measurement device 1A according to the present embodiment, first, a measurement subject 300 steps onto the platform unit 200 of the body fat measurement device 1A in the stored state. At this time, the measurement subject 300 brings the sole of his/her right foot 301 into contact with the foot electrode FR provided on the platform unit 200, and brings the sole of his/her left foot 302 into contact with the foot electrode FL provided on the platform unit 200.

Next, as shown in FIG. 7, the measurement subject 300 bends his/her upper body and assumes a squatting position, and grips the right-side frame portion 112 of the fitting unit 100A with his/her right hand 303 and the left-side frame portion 113 of the fitting unit 100A with his/her left hand 304. At this time, the measurement subject 300 brings the palm of his/her right hand 303 into contact with the hand electrode HR provided in the fitting unit 100A, and brings the palm of his/her left hand 304 into contact with the hand electrode HL provided in the fitting unit 100A.

Next, as shown in FIG. 8, the measurement subject 300 straightens his/her upper body while gripping the fitting unit 100A, and assumes a standing position. As this time, the measurement subject 300 does not change his/her foot placement, keeping the sole of his/her right foot 301 in contact with the foot electrode FR and the sole of his/her left foot 302 in contact with the foot electrode FL. Here, the measurement subject 300 lifts the fitting unit 100A by straightening his/her body, and the trunk area 305 of the measurement subject 300 is then positioned in the hollow opening area of the fitting unit 100A, surrounded by the frame member 110. Note that the connection cable 40 is pulled from the platform unit 200 when the fitting unit 100A is lifted.

Next, the measurement subject 300 adjusts the position of the fitting unit 100A by moving the fitting unit 100A in the direction of an arrow C in FIG. 8 while continuing to grip the fitting unit 100A, so that the front surface 121 of the electrode support member 120 provided in the fitting unit 100A is pressed against the back area surface (more specifically, against the surface of his/her hips on the back side).

At this time, the measurement subject 300 adjusts the pressure of the electrode support member 120 against his/her back area surface, and, while viewing and referring to the display unit 26B that displays the orientation of the fitting unit 100A in a visible state, adjusts the orientation of the fitting unit 100A so that the fitting unit 100A is positioned horizontally. To be more specific, the measurement subject 300 positions the fitting unit 100A horizontally by adjusting the angles of the right hand and left hand that grip the right-side frame portion 112 and left-side frame portion 113 of the frame member 110, adjusting the spatial positions where the right hand and left hand are placed, and so on. The measurement subject 300 maintains the horizontal orientation after adjusting the orientation of the fitting unit 100A.

As a result, the fitting unit 100A enters the fitted state shown in FIG. 9, and the measurement of body fat mass can be started. Here, in order to start the measurement of the body fat mass, the measurement subject 300 may depress the measure button 27a using the thumb of his/her right hand 303. Although descriptions have been omitted above, the measurement subject 300 is required to press the power button at an appropriate timing. Although the timing at which the power button is pressed is not particularly limited, it is preferable for the power button to be pressed before the measurement subject 300 assumes a squatting position and grips the fitting unit 100A.

As shown in FIG. 10, during the fitted state, when the fitting unit 100A is fitted to the measurement subject 300, the optical sensors 24A1 and 24A2 that correspond to the trunk area width detection unit 18A and the optical sensor 24B1 that corresponds to the trunk area depth detection unit 18B are positioned in the periphery of the trunk area 305, which includes the position of the navel of the measurement subject 300. Accordingly, the light emitted from the pair of optical sensors 24A1 and 24A2 corresponding to the width detection unit 18A can irradiate the right side surface of the trunk area 305 (in other words, the surface of the right flank area) and the left side surface of the trunk area 305 (in other words, the surface of the left flank area), respectively, of the measurement subject 300, whereas the light emitted from the optical sensor 24B1 for detecting the depth of the trunk area can irradiate the front surface of the trunk area 305 (in other words, the vicinity of the location of the navel in the abdominal area) of the measurement subject 300.

At this time, it is important for the fitting unit 100A to be kept in a horizontal orientation in order to accurately measure the trunk area width and trunk area depth using the optical sensors. Accordingly, in the body fat measurement device 1A according to the present embodiment, the aforementioned unit orientation detection unit 30 is provided in the fitting unit 100A, and the orientation of the fitting unit 100A as detected by the unit orientation detection unit 30 is displayed in a visible manner in the display unit 26B. In other words, the measurement subject 300 can be guided by viewing the display unit 26B and using the display unit 26B as a reference for maintaining the orientation of the fitting unit 100A in a horizontal orientation.

Trunk Dimension Measurement

Here, in the range measurement performed using the optical sensors 24A1, 24A2, and 24B1 that serve as range sensors, light is irradiated from a light source (an LED (light emitting diode), a laser diode, or the like) located within the sensor. The irradiated light is reflected by the surface of the body, and the reflected light is then received by a light-receiving element within the sensor. A PSD (position-sensitive detector) or the like is used as the light-receiving element. The optical sensor takes an image forming position of the light-receiving element resulting from a change in the distance between the light-receiving element and the surface of the body, converts the position into a distance, and outputs that distance. Alternatively, the time from when the light is emitted until the light is received is measured, and that time is converted into a distance and outputted.

As shown in FIG. 10, a width 2a of the trunk area 305 of the measurement subject 300 is calculated by the width detection unit 18A using a distance A1 (that is, the distance between the right-side frame portion 112 and the right side surface of the trunk area 305 of the measurement subject 300) and a distance A2 (that is, the distance between the left-side frame portion 113 and the left side surface of the trunk area 305 of the measurement subject 300) detected by the pair of optical sensors 24A1 and 24A2 for detecting the trunk area width, along with a predetermined distance A (that is, the distance between the right-side frame portion 112 and the left-side frame portion 113). Likewise, a depth 2b of the trunk area 305 of the measurement subject 300 is calculated by the depth detection unit 18B using a distance B1 detected by the optical sensor 24B1 (that is, the distance between the rear surface of the display unit portion 130 and the front surface of the trunk area 305 of the measurement subject 300) and a predetermined distance B (that is, the distance between the rear surface of the display unit portion 130 and the center of the front surface 121 of the electrode support member 120 in the horizontal direction). The body shape information measurement unit 18 stores the calculated width $2a$ and depth $2b$ in the memory unit 29.

Here, the noise removal unit 24 includes a LPF (low pass filter), takes voltage signals outputted from the optical sensors 24A1, 24A2, and 24B1 as inputs, uses the LPF to remove noise components (high-frequency signal components) contained in the inputted voltage signals, and outputs the resulting signals to the control unit 100. Through this, the distances B1, A1, and A2 can be measured accurately.

In addition to the stated optical sensors, it should be noted that various types of non-contact range sensors that use ultrasound waves or electromagnetic waves (light of various wavelength ranges including laser light, visible light, and so on, radio waves, magnetism, electrical fields, and the like) can also be employed as the range sensors used to detect the width and depth of the trunk area.

When measuring the aforementioned distances, assuming that the orientation of the fitting unit 100A is not being maintained in a horizontal orientation, the fitting unit 100A will tilt, causing the stated distance B1, distance B2, and distance A1 to be incorrectly measured, which in turn leads to problems such as the width $2a$ and the depth $2b$ containing errors or that the trunk area width and depth cannot be measured at all. These problems can be eliminated through the following.

Fitting Unit Orientation Display

Figure 11:
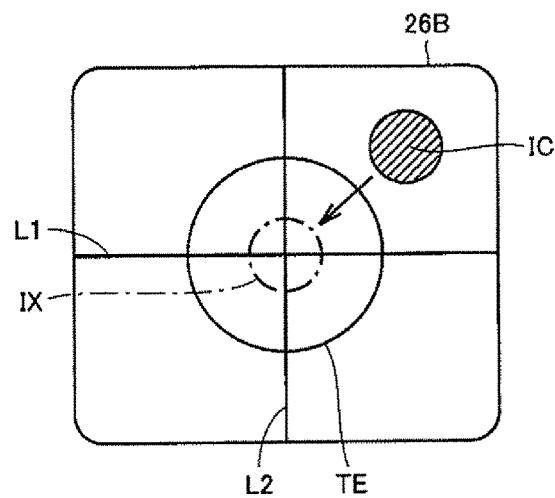
FIG. 11 is a diagram illustrating an example of a display of the orientation of the fitting unit of the body fat measurement device according to the embodiment of the present invention.

FIG. 11 is a diagram illustrating an example of a display in the display unit that displays the orientation of the fitting unit of the body fat measurement device according to the present embodiment. Next, an example of the display in the display unit that displays the orientation of the fitting unit of the body fat measurement device according to the present embodiment will be described with reference to FIG. 11.

As shown in FIG. 11, with the body fat measurement device 1A according to the present embodiment, guidance information that is based on a result of the detection performed by the unit orientation detection unit 30 is displayed in the guide unit 10 so that the measurement subject can instinctively recognize the orientation of the fitting unit 100A.

To be more specific, a guide line L1 that represents the horizontal direction of the fitting unit 100A and a guide line L2 that represents the depth direction of the fitting unit 100A are indicated in the display screen of the display unit 26B, and furthermore, a region TE expressing a permissible range of the orientation of the fitting unit 100A is indicated, in an ancillary manner, as a circle in the center of which the guide line L1 and the guide line L2 intersect. An indicator IC, expressing the result of the detection performed by the unit orientation detection unit 30, is shown in the screen as, for example, a circle.

Here, the display state shown in FIG. 11 indicates that a right-front area of the fitting unit 100A (that is, the area of connection between the right-side frame portion 112 and the front frame portion 114) is lower than the other areas, and thus the measurement subject adjusts the orientation of the fitting unit 100A so that the indicator IC falls within the aforementioned region TE that expresses the permissible range (that is, so that the indicator IC moves to the position indicated by IX, shown as a broken circle in FIG. 11).

Processes for Body Fat Measurement

Figure 12:
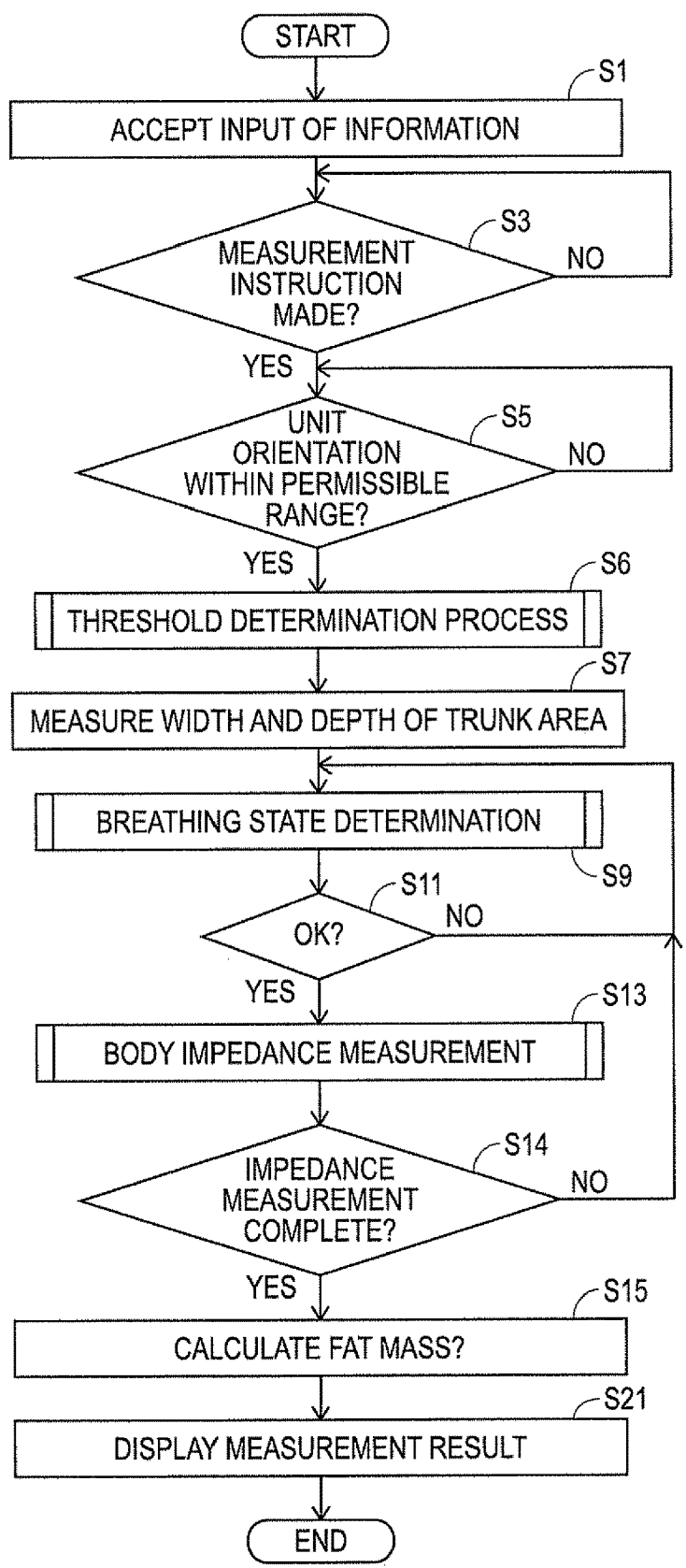
FIG. 12 is process flowchart of the body fat measurement device according to the embodiment of the present invention.
Figure 13:
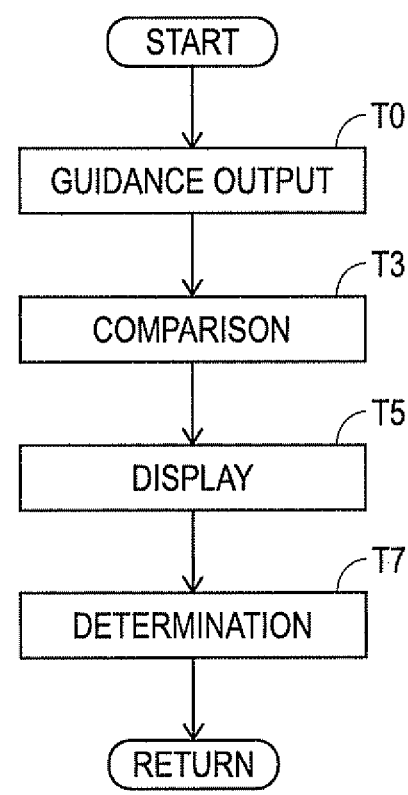
FIG. 13 is process flowchart for a breathing state determination according to the embodiment of the present invention.
Figure 14:
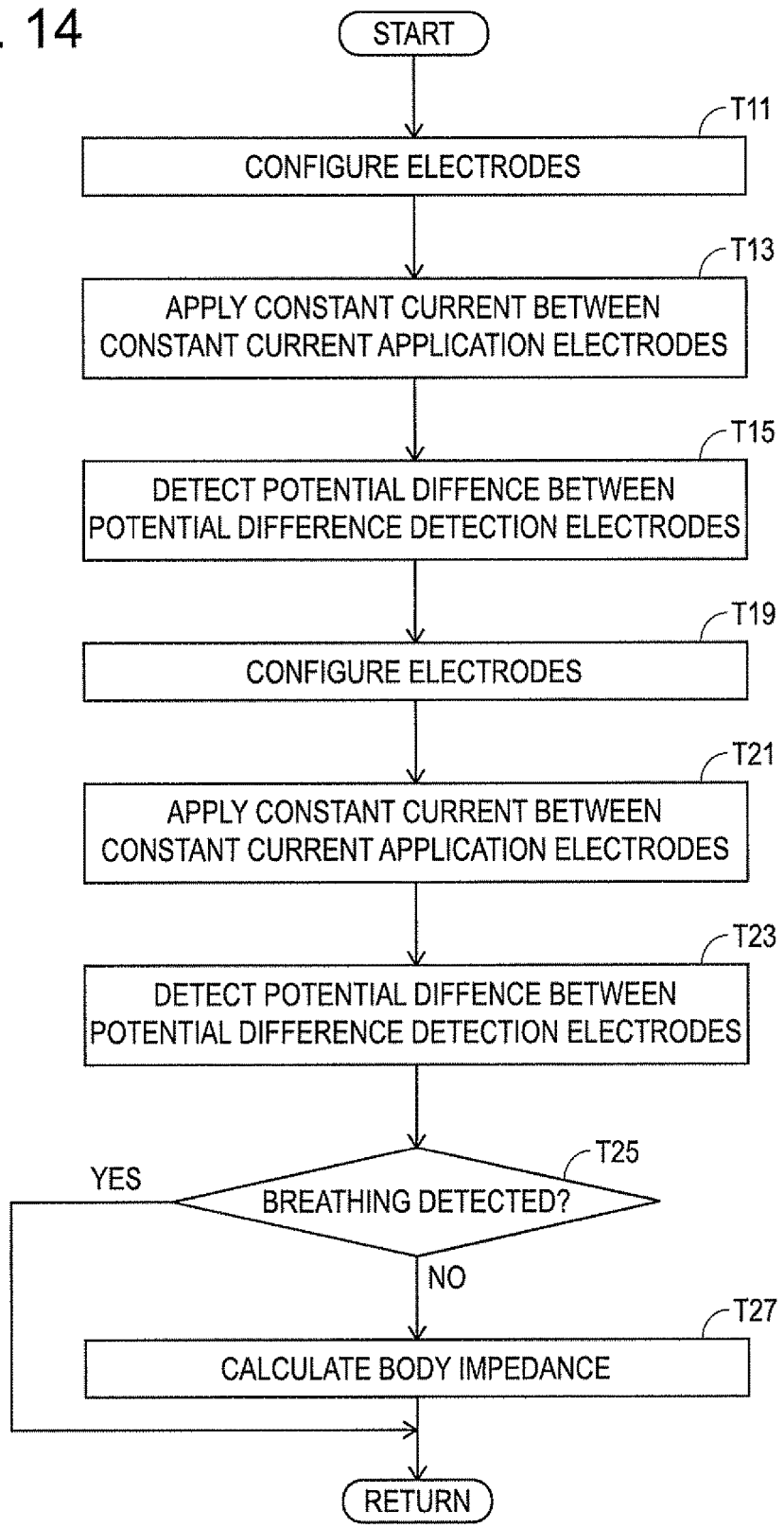
FIG. 14 is process flowchart for a body impedance measurement according to the embodiment of the present invention.
Figure 15:
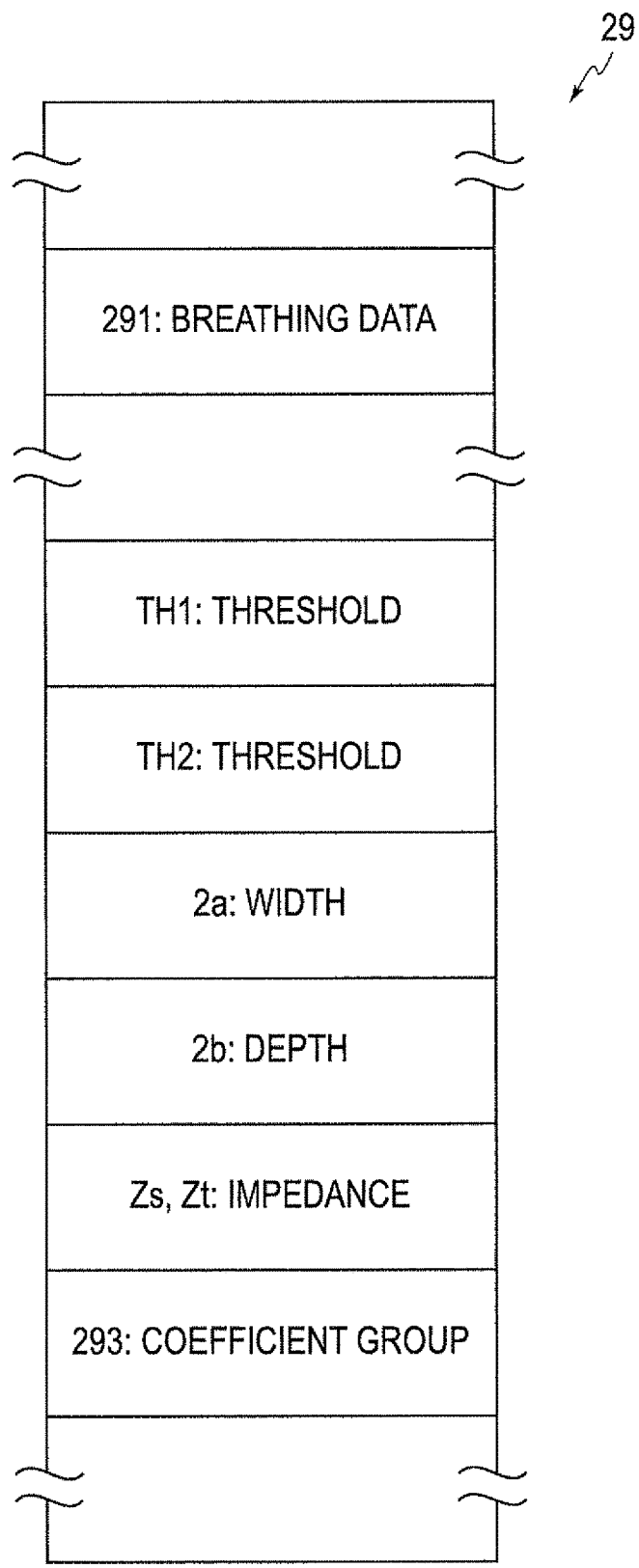
FIG. 15 is a diagram illustrating an example of the content of a memory unit of the body fat measurement device according to the embodiment of the present invention.
Figure 16:
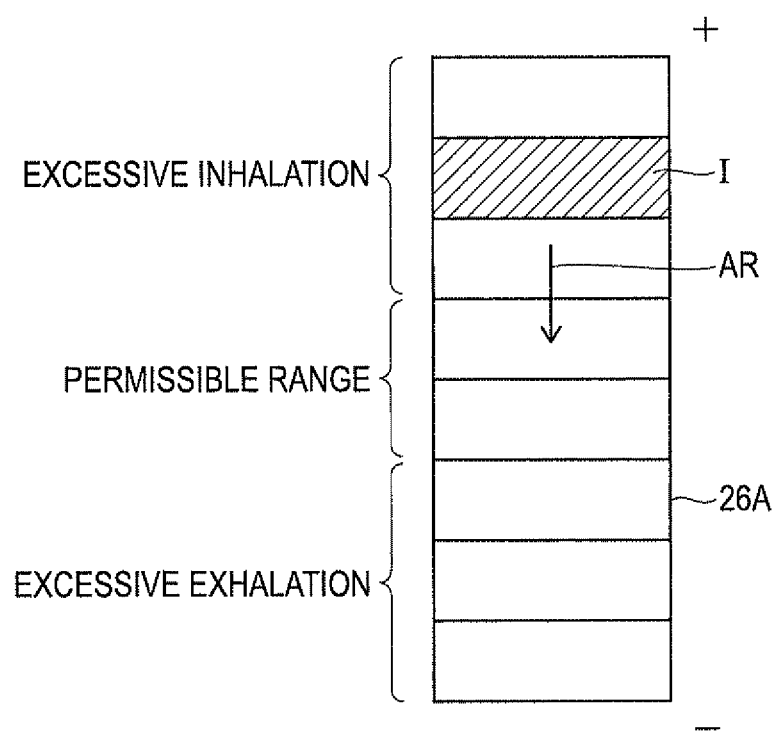
FIG. 16 is a diagram illustrating an example of the display of guidance information according to the embodiment of the present invention.

The processes for body fat measurement performed by the body fat measurement device 1A will be described using FIGS. 12 through 20. FIGS. 12 to 14 illustrate flowcharts of the measurement process, and FIG. 15 illustrates an example of content stored in the memory unit 29. FIG. 16 illustrates an example of the guidance information displayed during the body fat measurement in order to enable the breathing state to transit to a state that is suited for measurement.

Note that the processes indicated in the flowchart in FIGS. 12 through 14 are stored in the memory unit 29 in advance as programs, and a visceral fat cross-sectional area measurement process and a subcutaneous fat cross-sectional area measurement process are realized by the control unit 100 when the control unit 100 including the computation processing unit 15 reads out and executes those programs.

In addition to breathing data 291, which is illustrated in FIG. 15 and will be mentioned later, and data of the coefficient group 293 and the thresholds TH1 and TH2, the measured trunk area width $2a$ and depth $2b$, the measured body impedances Zs and Zt, the measurement subject information and calculated body composition information, a body composition information measurement program/data for executing a body composition information measurement process, which will be mentioned later, and so on are stored in the memory unit 29.

FIGS. 17 through 20 are diagrams schematically illustrating a procedure for determining a threshold used for determining the breathing state during the body fat measurement.

Estimation of Breathing State

First, a process for estimating the breathing state of the measurement subject, performed by the breathing estimation unit 11, will be described.

When the measure button 27a is operated and the measurement process is commenced, the breathing estimation unit 11 begins estimating the breathing state of the measurement subject.

Specifically, based on an instruction from the control unit 100, the optical sensor 24B1 cyclically irradiates the front surface of the trunk area 305 (that is, the vicinity of the location of the navel in the abdominal area) of the measurement subject 300 with light. The irradiated light reflects off the front surface of the trunk area 305. Through this, the optical sensor 24B1 cyclically receives the irradiated light reflected off the front surface of the trunk area 305. A voltage signal indicating the distance B1 is outputted based on a signal representing the light received by the optical sensor 24B1. The voltage signal undergoes noise removal by the noise removal unit 24, and is then outputted to the breathing estimation unit 11. The breathing estimation unit 11 inputs the voltage signal outputted from the noise removal unit 24 in time series, based on time measurement data from the timer unit 20. The voltage signal inputted in time series is then converted to digital data, and the converted time series data is then stored in the memory unit 29 as the breathing data 291. Accordingly, the breathing estimation unit 11 estimates the breathing state of the measurement subject by obtaining time series data of the distance B1 measured using the optical sensor 24B1, or in other words, by obtaining the breathing data 291 indicating changes in the depth $2b$ resulting from the expansion/contraction of the abdominal area caused by breathing.

Note that it is assumed that the breathing data 291, which is time series data of the distance B1 measured using the optical sensor 24B1, continues to be obtained during the period spanning from when the breathing estimation unit 11 begins measurement to when at least the body impedance measurement or the body fat calculation is complete.

Threshold Determination Process

Figure 17:
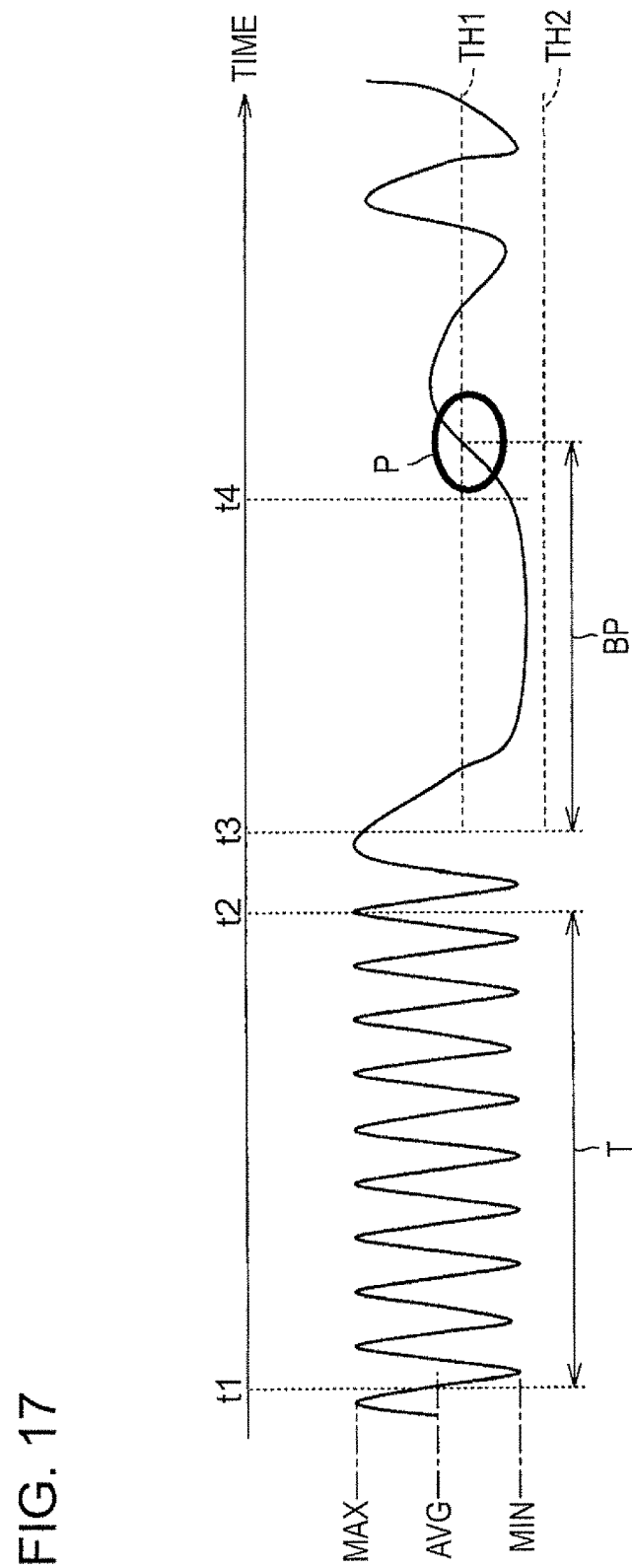
FIG. 17 is a diagram illustrating a threshold determination process according to the embodiment of the present invention.
Figure 18:
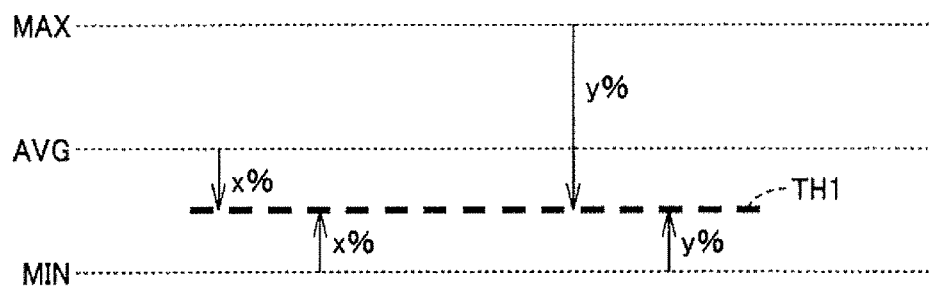
FIG. 18 is a diagram illustrating a threshold determination process according to the embodiment of the present invention.
Figure 19:
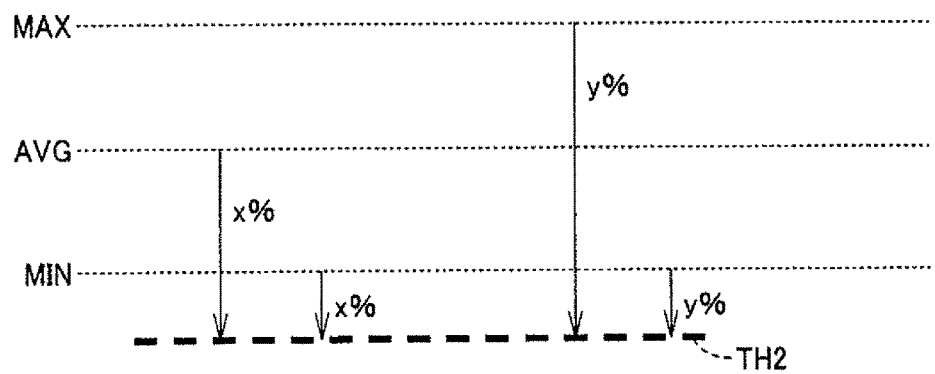
FIG. 19 is a diagram illustrating a threshold determination process according to the embodiment of the present invention.

A procedure for determining a threshold to be used for determining the breathing state during measurement will be described with reference to FIGS. 17 through 21. FIG. 17 schematically illustrates an example of the breathing data 291, and FIGS. 18 and 19 illustrate a specific method for determining a threshold.

When the threshold determination process is started by the threshold determination unit 12D after the measurement has started, the guide unit 10 outputs the guidance information regarding the breathing state to the display unit 26A. First, guidance information prompting the measurement subject to control his/her breathing and transit to the stable breathing state is outputted. The measurement subject controls his/her breathing based on the displayed guidance information, so as to transit his/her breathing to a stable state.

After the guidance information for prompting the stable breathing state has been displayed, the breathing stability determination unit 12C determines, based on the breathing data 291 in the memory unit 29, whether or not a state in which the amplitude/cycle of a waveform indicated by the breathing data 291 (that is, the magnitude of changes in the depth 2b resulting from the expansion/contraction of the abdominal area caused by breathing, and the cycle of those changes) are approximately constant, or in other words, the stable breathing state, has continued for a predetermined amount of time.

Here, the breathing stability determination unit 12C determines that the breathing is in a stable breathing state when a state in which the amplitude/cycle of the waveform is constant has continued for a predetermined period T.

When it has been determined that the breathing is in the stable breathing state, the guide unit 10 displays, in the display unit 26A, guidance information prompting the measurement subject to exhale and stop breathing in the exhaled state.

Based on the guidance information, the measurement subject exhales and stops breathing in the exhaled state. After this, the guide unit 10 outputs guidance prompting the measurement subject to breathe, via the display unit 26A. Based on this guidance, the measurement subject resumes breathing from the breathing-stopped state.

In this manner, the breathing data 291 (FIG. 17) indicating changes in the distance B1 is obtained by the breathing estimation unit 11 during the period in which the measurement subject changes his/her breathing state in accordance with the guidance information from the guide unit 10.

Changes in the distance B1 occurring with the passage of time are illustrated in FIG. 17. According to FIG. 17, the breathing is in the stable breathing state (that is, the amplitude/cycle are approximately constant) for the predetermined period T spanning from times t1 to t2 following the start of measurement; however, after this, at a time t3, the measurement subject begins to exhale, and stops breathing. When breathing is resumed at a time t4 thereafter, or in other words, when the measurement subject begins to inhale, breathing is resumed at a time corresponding to a point P following thereafter. Accordingly, a time spanning from the time t3 to the point P in FIG. 17 indicates a breathing-stopped state BP.

The threshold determination unit 12D determines the thresholds TH1 and TH2 based on the breathing data 291 indicated in FIG. 17. The thresholds TH1 and TH2 are used for determining whether the measurement subject is in the breathing-stopped state BP, a breathing state, or an excessive exhalation state. FIG. 18 schematically illustrates a method for determining the threshold TH1, whereas FIG. 19 schematically illustrates a method for determining the threshold TH2.

The method for determining the threshold TH1 will be described with reference to FIG. 18.

The threshold determination unit 12D calculates a base value (a maximum value MAX and a minimum value MIN of the amplitude) by performing a differential process on a waveform (see FIG. 17) indicating data of the breathing data 291 that corresponds to the predetermined period T, and calculates a median value, or in other words, an average value AVG of the maximum value MAX and the minimum value MIN. Then, the amplitude value of the waveform indicating the breathing data 291 that corresponds to the predetermined period T is multiplied by a predetermined coefficient for calculating the thresholds, and computations are carried out using the result of the multiplication and the base value. The respective values resulting from the computations are set as the threshold TH1.

Specifically, an average value of the amplitudes of the respective waveforms obtained during the predetermined period T is calculated, and the result of subtracting a value equivalent to y % of the calculated average amplitude value from the maximum value MAX or the result of adding a value equivalent to y % of the calculated average amplitude value to the minimum value MIN is set as the threshold TH1.

Alternatively, the average value of the amplitudes in an approximate half-cycle of the respective waveforms obtained during the predetermined period T is calculated, and the result of subtracting a value equivalent to x % of the calculated average amplitude value from the average value AVG or the result of adding a value equivalent to x % of the calculated average amplitude value to the minimum value MIN is set as the threshold TH1.

Next, the method for determining the threshold TH2 will be described with reference to FIG. 19.

First, the base value (that is, the average value AVG of the maximum value MAX and the minimum value MIN) is calculated as mentioned above. Then, an average value of the amplitudes of the respective waveforms obtained during the predetermined period T is calculated, and the result of subtracting a value equivalent to y % of the calculated average amplitude value from the maximum value MAX or the result of adding a value equivalent to y % of the calculated average amplitude value to the minimum value MIN is set as the threshold TH2.

Alternatively, the average value of the amplitudes in an approximate half-cycle of the respective waveforms obtained during the predetermined period T is calculated, and the result of subtracting a value equivalent to x % of the calculated average amplitude value from the average value AVG or the result of adding a value equivalent to x % of the calculated average amplitude value to the minimum value MIN is set as the threshold TH2.

Note that the predetermined coefficients for calculating the thresholds TH1 and TH2 (y %, x %) are detected in advance through experimentation and stored in the memory unit 29 as the coefficient group 293, and thus the threshold determination unit 12D can calculate the thresholds using the predetermined coefficients (y %, x %) read out from the memory unit 29. The calculated thresholds TH1 and TH2 are stored in the memory unit 29.

Although the stated thresholds TH1 and TH2 are described as being calculated using the maximum value MAX and the minimum value MIN based on the breathing data 291 obtained during the predetermined period T, it should be noted that the calculation method is not limited thereto.

Figure 20:
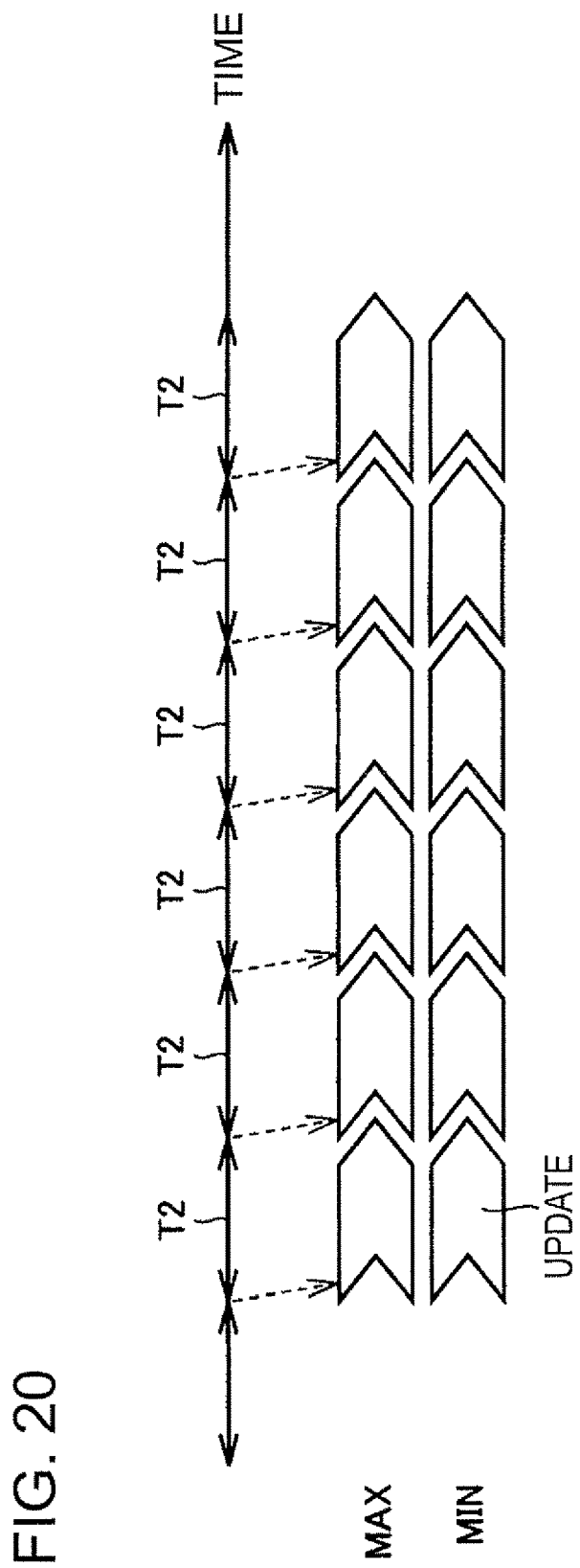
FIG. 20 is a diagram illustrating a threshold determination process according to the embodiment of the present invention.

For example, as shown in FIG. 20, the predetermined period T can be divided into multiple periods T2, and the maximum value MAX and minimum value MIN are then calculated for each period T2 based on the breathing data 291 obtained during that period T2. Then, the maximum value MAX and minimum value MIN obtained during the period T2 immediately previous is updated using the maximum value MAX and minimum value MIN calculated during the following period T2. The average value AVG is then calculated using the maximum value MAX and minimum value MIN that are ultimately calculated. The thresholds TH1 and TH2 may then be calculated thereafter.

Normalization Process

The thresholds TH1 and TH2 are not limited to the aforementioned calculation methods. In other words, although the thresholds TH1 and TH2 are calculated based on the amplitude value of the waveform of the breathing data 291, the amplitude values vary based on differences in the way each measurement subject breathes, and thus using the fixed predetermined coefficients (y %, x %) may result in variations in the determination of stopped breathing based on the thresholds TH1 and TH2 and in the basis of breathing determination for each measurement subject; this can make it difficult to obtain a suitable precision for the measurement.

Accordingly, to eliminate these variations, the normalizing unit 11A of the breathing estimation unit 11 corrects the amplitude that is based on the breathing data 291 of the measurement subject using a coefficient G read out from the coefficient group 293 of the memory unit 29. Specifically, as shown in FIG. 21, an amplitude X of a waveform based on the breathing data 291 is normalized by multiplying that amplitude X by the coefficient G. Using the normalized amplitude A makes it possible to apply the appropriate thresholds TH1 and TH2 for determining the breathing state, irrespective of the measurement subject in question.

Meanwhile, because the predetermined coefficients (y %, x %) are fixed predetermined coefficients, using the normalized amplitude A makes it possible to employ the thresholds TH1 and TH2 as shared thresholds for multiple measurement subjects; this in turn makes it possible to omit processes for determining the thresholds TH1 and TH2.

Note that the method for determining the coefficient G used for normalizing the amplitude can be set through learning. In other words, the amplitude of a waveform based on the breathing data 291 detected during the stable breathing state is measured for each measurement subject for a set amount of time, and the coefficient G that brings an amplitude value X measured during the set amount of time to a predetermined value A is then calculated. In this manner, the coefficient G can be determined for respective measurement subjects.

Overall Processing

The processes performed by the body fat measurement device during measurement will be described using FIGS. 12 through 14. Note that it is assumed that during the measurement, the fitting unit 100A is fitted to the measurement subject as shown in FIG. 9.

As shown in FIG. 12, the control unit 100 first accepts an input of the measurement subject information (step S1). The accepted measurement subject information is temporarily stored in, for example, the memory unit 29.

Next, the control unit 100 determines whether or not there has been an instruction to start the measurement (step S2). The control unit 100 stands by until there has been an instruction to start the measurement (NO in step S2), and advances to the next process in the case where an instruction to start the measurement has been detected (YES in step S2). Note that the instruction to start the measurement is made by the measurement subject depressing the measure button 27a.

Next, the control unit 100 determines whether or not the orientation of the fitting unit 100A is within the permissible range (in other words, whether or not the fitting unit 100A is in a horizontal orientation) (step S3). Specifically, in the case where it has been determined that the fitting unit 100A is not within the stated permissible range based on a signal inputted from the unit orientation detection unit 30 (NO in step S3), the control unit 100 stands by until the fitting unit 100A is within the permissible range. At this time, control prompting the measurement subject to adjust the orientation of the fitting unit 100A, warning the measurement subject that the orientation of the fitting unit 100A is not in a horizontal orientation by emitting a warning sound, or the like may be carried out by the guide unit 10 displaying guidance, such as that shown in FIG. 11, in the display unit 26B. On the other hand, in the case where it has been determined that the fitting unit 100A is within the permissible range based on a signal inputted from the unit orientation detection unit 30 (YES in step S3), the control unit 100 moves to the next process.

In the present embodiment, the aforementioned threshold determination process is carried out by the threshold determination unit 12D when it has been determined that the breathing of the measurement subject is suited to measurement (step S6).

Next, the control unit 100 measures the width and depth of the trunk area (step S7). Specifically, the guide unit 10 displays, in the display unit 26A, guidance information prompting the measurement subject to exhale and then stop breathing. The measurement subject exhales and stops breathing in accordance with the guidance information. In this state, the body shape information measurement unit 18 obtains the width 2a and depth 2b of the measurement subject's trunk area based on signals from the optical sensors 24A1, 24A2, and 24B1. The obtained width 2a and depth 2b of the measurement subject's trunk area are temporarily stored in the memory unit 29.

Next, the process for determining whether or not the measurement subject's breathing is in a state that is suitable for measuring body fat (see FIG. 13) is carried out by the breathing state determination unit 12 (step S9). The breathing data 291 obtained by the breathing estimation unit 11 is used in this breathing state determination process. The breathing data 291 indicates time series changes in the distance B1 (the depth 2b) based on the output of the optical sensor 24B1. The process of step S9 will be described in detail later.

When the control unit 100 determines that the breathing of the measurement subject is not in a state that is suited to measurement based on the result of the determination performed by the breathing state determination unit 12 (NO in step S11), the process returns to step S9. Accordingly, the process of step S9 is repeated during the period in which it is determined that the breathing is not in a state that is suited to measurement. The breathing state of the measurement subject transits to a state that is suited to measurement as a result of this repetition.

When it is determined that the breathing state is a state that is suited to measurement (YES in step S11), a body impedance measurement, mentioned later, is carried out by the body impedance measurement unit 16 (step S13).

The breathing determination unit 12B determines whether or not the breathing of the measurement subject is detected during the procedure by which the body impedance measurement unit 16 measures the body impedance. In other words, the breathing determination unit 12B reads out the breathing data 291 obtained by the breathing estimation unit 11 and the threshold TH1 from the memory unit 29, and compares the value of the read-out breathing data 291 with the threshold TH1. When it is determined that the value of the breathing data 291 is greater than the threshold TH1 (see FIG. 17) based on the result of the comparison, it is determined that the breathing of the measurement subject has been detected. When the breathing of the measurement subject has been detected, the measurement of the body impedance is suspended, and thus a measurement result is not obtained. In other words, the impedance measurement is determined to be incomplete (NO in step S14). In this case, the process moves to step S9. After this, the processes of steps S9 and S11 are carried out, and the body impedance is once again measured by the body impedance measurement unit 16 (step S13). The body impedances Zt and Zs calculated as a result of the measurement are stored in the memory unit 29.

In this manner, when the breathing determination unit 12B has determined that the measurement subject is breathing while the body impedance is being measured, the measurement of the body impedance is suspended, and the body impedance measurement is started once again. Through this, the contraction/expansion of abdominal area structures caused by breathing can be prevented from influencing the measured body impedance.

After the measurement of the body impedance in step S13 is complete (YES in step S14), the calculation control unit 13 instructs the body composition information obtainment unit 17 to begin calculations. When this instruction is inputted, the body composition information obtainment unit 17 controls the visceral fat mass calculation unit 17A and the subcutaneous fat mass calculation unit 17B to begin calculating the fat masses (step S15).

Specifically, the width 2a and depth 2b of the trunk area detected in step S7 and the body impedances Zt and Zs calculated in step S13 are read out from the memory unit 29, and based on these read-out values, the visceral fat cross-sectional area Sx is calculated as the visceral fat mass by the visceral fat mass calculation unit 17A, and the subcutaneous fat cross-sectional area Sb is calculated as the subcutaneous fat mass by the subcutaneous fat mass calculation unit 17B. The calculated visceral fat cross-sectional area Sx and subcutaneous fat cross-sectional area Sb are stored in the memory unit 29.

When the calculation of the fat masses ends, the results of the calculations, or in other words, fat mass information, is displayed in the display unit 26 (step S21).

The measurement process then ends.

In the process shown in FIG. 12, the process for obtaining the thresholds TH1 and TH2 (step S6) is executed each time during measurement even if the measurement subject is the same; however, it should be noted that this process need not be executed each time. In other words, in the case where the thresholds TH1 and TH2 have been obtained in step S6 during the initial measurement, the process of step S6 may be omitted from the second and subsequent measurements, and the thresholds TH1 and TH2 obtained the initial time may then be used as the thresholds for determining the breathing state. Alternatively, whether or not to omit the process may be selected as appropriate by the measurement subject operating the operating unit 27.

Breathing State Determination Process

The breathing state determination process (step S9) will now be described with reference to FIG. 13.

First, the guide unit 10 outputs, through the display unit 26A, guidance information for guiding the measurement subject to breathe in a manner that is suited to measurement (step T0).

Specifically, the guidance information prompts the measurement subject to control his/her breathing and transit to the stable breathing state. Thereafter, the breathing stability determination unit 12C determines whether or not the amplitude/cycle of the waveform indicated by the breathing data 291 is approximately constant, based on the breathing data 291 in the memory unit 29. When it has been determined that the amplitude/cycle of the waveform is constant, it is determined the breathing is in the stable breathing state.

When it is determined that the breathing is in the stable breathing state, the guide unit 10 displays guidance information prompting the measurement subject to exhale and stop breathing after exhaling. Having confirmed the guidance information, the measurement subject exhales and stops breathing.

When the guidance information prompting the measurement subject to stop breathing is displayed, the breathing stop determination unit 12A reads out the breathing data 291 and the thresholds TH1 and TH2 from the memory unit 29. The breathing data 291 is then compared with the thresholds TH1 and TH2 (step T3).

Based on the result of this comparison, the guide unit 10 displays guidance information in the display unit 26A (step T5). FIG. 16 illustrates an example of this display. Details of FIG. 16 will be given later.

Next, the breathing stop determination unit 12A determines whether or not the breathing data 291 indicates a value that is within the range of the thresholds TH1 and TH2, based on the result of the comparison. In other words, it is determined whether or not the measurement subject has exhaled and stopped breathing (the breathing-stopped state BP indicated in FIG. 17), or in other words, whether or not the state is one that is suited to measurement (step T7).

This concludes the breathing state determination process.

Body Impedance Measurement

FIG. 14 illustrates a detailed procedure of the body impedance measurement performed by the body impedance measurement unit 16 (step S13).

In FIG. 14, first, the control unit 100 configures the electrodes (step T11). Specifically, the control unit 100 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1A.

Next, the control unit 100 applies a constant current between the constant current application electrodes (step T13). Specifically, the control unit 100 outputs an instruction to the constant current generation unit 21 for generating the constant current, and based on this, the constant current generation unit 21 applies the generated constant current $I_A$ between the constant current application electrodes as shown in FIG. 1A.

Next, the control unit 100 detects a potential difference between the potential difference detection electrodes (step T15). Specifically, the control unit 100 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 16.

Next, the control unit 100 reconfigures the electrodes (step T19). Specifically, the control unit 100 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1B.

Next, the control unit 100 applies a constant current between the constant current application electrodes (step T21). Specifically, the control unit 100 outputs an instruction to the constant current generation unit 21 for generating the constant current, and based on this, the constant current generation unit 21 applies the generated constant currents $I_{B1}$ and $I_{B2}$ between the constant current application electrodes as shown in FIG. 1B.

Next, the control unit 100 detects a potential difference between the potential difference detection electrodes (step T23). Specifically, the control unit 100 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

The breathing determination unit 12B compares the breathing data 291 and the threshold TH1 read out from the memory unit 29. When the value of the breathing data 291 is determined to be greater than the threshold TH1 (see FIG. 17) based on the result of the comparison, it is determined that the measurement subject is breathing during the impedance measurement (YES in step T25). In this case, the procedure returns to the process of FIG. 13 without the body impedance calculations mentioned later being carried out.

When the breathing determination unit 12B determines that the value of the breathing data 291 is greater than or equal to the threshold TH2 and less than or equal to the threshold TH1 based on the result of the comparison, or in other words, that the breathing is in a stopped state (NO in step T25), the body impedance is calculated in step T27. In this manner, when breathing is detected during the body impedance measurement, the body impedance is not calculated, and thus changes in the positions of internal organs caused by breathing can be suppressed from influencing the calculated body impedance.

In step T27, the control unit 100 calculates the body impedances Zt and Zs. Specifically, the body impedance measurement unit 16 calculates the body impedance Zt based on the potential differences $V_{A1}$, $V_{A2}$, $V_{A3}$, and $V_{A4}$ inputted from the potential difference detection unit 23. The calculated body impedance Zt is temporarily stored in the memory unit 29. The body impedance measurement unit 16 then calculates the body impedance Zs based on $V_{B1}$ and $V_{B2}$ inputted from the potential difference detection unit 23. The calculated body impedance Zs is temporarily stored in the memory unit 29. After this, the procedure returns to the process of FIG. 13.

Because the body impedance should be measured during a breathing-stopped state (this corresponds to the breathing-stopped state BP in FIG. 17), when the breathing of the measurement subject is detected (YES in step T25), the measurement of the body impedance is suspended and the body impedance measurement is started once again in the aforementioned procedure; this may be carried out as follows. That is, when the body impedance is measured and the breathing of the measurement subject is detected, the calculation of the fat mass using the measured body impedance may be suspended, and the body impedance measurement and fat mass calculation may then be started once again.

In other words, the breathing determination unit 12B determines whether or not the breathing of the measurement subject has been detected, in the same manner as described above, while the visceral fat mass calculation unit 17A and the subcutaneous fat mass calculation unit 17B calculate the fat masses. When it is determined that breathing has been detected, the recalculation control unit 14 instructs the body composition information obtainment unit 17 to suspend the calculations. In response to this instruction, the body composition information obtainment unit 17 controls the visceral fat mass calculation unit 17A and the subcutaneous fat mass calculation unit 17B to suspend the operations for calculating the fat masses. Through this, the visceral fat mass calculation unit 17A and the subcutaneous fat mass calculation unit 17B suspend the operations for calculating the fat masses currently being carried out. After this, the procedure moves through steps S9 and S11, after which the body impedance is once again measured in step S13, and the visceral fat mass calculation unit 17A and subcutaneous fat mass calculation unit 17B once again start the calculations of the fat masses in step S15.

Through this, breathing can be suppressed from influencing the calculated fat masses.

Example of Guidance Display for Stable Breathing State

An example of the display of the guidance information performed by the guide unit 10 for prompting the measurement subject to transit his/her breathing to the stable breathing state (step T5 of FIG. 13) will be described with reference to FIG. 16.

In FIG. 16, multiple rectangular pictograms are arranged in a column. Text indicating the breathing state, reading "permissible range", "excessive inhalation", and "excessive exhalation" are displayed in correspondence with the pictogram column. When it is determined, based on the result of the comparison, that the value of the breathing data 291 indicates a value within the range of the thresholds TH1 and TH2, the pictogram corresponding to "permissible range" lights up, but if it is determined that the value is greater than the threshold TH1, the pictogram corresponding to "excessive inhalation" lights up, whereas if it is determined that the value is lower than the threshold TH2, the pictogram corresponding to "excessive exhalation" lights up.

Note that the display is not limited to the three levels of "permissible range", "excessive inhalation", and "excessive exhalation". For example, sets of multiple pictograms may be disposed in correspondence with "permissible range", "excessive inhalation", and "excessive exhalation", respectively, and one of the pictograms within one of the sets may light up in accordance with the magnitude of the difference between the value of the breathing data 291 and the thresholds TH1 and TH2. FIG. 16 illustrates a state in which, of three pictograms corresponding to "excessive inhalation", the second pictogram I is lighted up in accordance with the magnitude of the difference from the threshold TH1.

Meanwhile, as shown in FIG. 16, by simultaneously displaying an arrow AR that indicates a pictogram in the "permissible range", the measurement subject can be prompted to control his/her breathing so that a pictogram in the direction of the arrow AR lights up.

According to the display illustrated in FIG. 16, changes in the breathing (excessive exhalation or inhalation) can be presented as an indicator.

Variations

Although changes in the distance B1 over time (that is, changes in the trunk area depth 2b over time) are detected here as changes over time in the shape of the side cross-section of the region of the trunk area that corresponds to the position of the navel, the detection of changes in the shape of the trunk area is not limited thereto.

For example, the breathing estimation unit 11 calculates the shape of the trunk area based on the distances A1, A2, and B1 measured using the optical sensors 24A1, 24A2, and 24B1, and based on the width 2a and the depth 2b. Then, the changes over time in the shape of the trunk area are detected based on the calculated changes over time of the shape of the trunk area, and more specifically, the changes of time in the area of the side cross-section of the trunk area; the breathing data 291 may then be obtained based on the result of the detection.

Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

REFERENCE SIGNS LIST 1A body fat measurement device
2a trunk area width
2b trunk area depth
10 guide unit
11 breathing estimation unit
11A normalization unit
12 breathing state determination unit
12A breathing stop determination unit
12B breathing determination unit
12C breathing stability determination unit
12D threshold determination unit
13 calculation control unit
14 recalculation control unit
15 computation processing unit
16 body impedance measurement unit
17 body composition information obtainment unit
17A visceral fat mass calculation unit
17B subcutaneous fat mass calculation unit
18 body shape information measurement unit
18A width detection unit
18B depth detection unit
21 constant current generation unit
22 terminal switching unit
23 potential difference detection unit
24 noise removal unit
24A1, 24A2, 24B1 optical sensor information input unit
26, 26A, 26B display unit
27 operating unit
27a measure button
29 memory unit
30 unit orientation detection unit
100 control unit
100A fitting unit
291 breathing data
293 coefficient group
BU1-BU4, BL1-BL4 back area electrode

The invention claimed is:

1. A body fat measurement device comprising:
multiple electrodes configured for making contact with a surface of a measurement subject's body at a measurement subject's trunk area;
a non-contact range sensor that measures a distance to a surface of the measurement subject's trunk area and outputs a signal indicating the measured distance;
a display;
a frame member to which the display is attached, the frame member comprising a plurality of rod-shaped portions connected with each other such that, when the body fat measurement device is in use, the connected rod-shaped portions are placed to surround the measurement subject's trunk area and to be gripped by the measurement subject; and
a processor programmed to:
input the signal outputted by the non-contact range sensor in time series;
measure a dimension of the measurement subject's trunk area based on a signal waveform expressed by the inputted time-series signal;
measure a shape of the measurement subject's trunk area based on the measured dimension of the measurement subject's trunk area;
detect a change over time in the trunk area shape and estimate a breathing of the measurement subject based on the detected change;
determine whether or not the estimated breathing is in a stopped state in which the measurement subject has stopped breathing after exhaling, based on a result of comparing an amount of change in the measured dimension of the measurement subject's trunk area with an amount of change in the dimension of the measurement subject's trunk area during the stopped state that has been detected in advance;
cause the display to display a state of the estimated breathing in association with a result of determining whether the estimated breathing is in the stopped state;
start measuring a body impedance of the measurement subject using the multiple electrodes when the estimated breathing is determined to be in the stopped state; and
calculate a trunk area fat mass using the measured body impedance and a trunk area size based on the measured shape of the measurement subject's trunk area.

2. The body fat measurement device according to claim 1, wherein the processor is programmed to:
when the measurement subject is determined to be breathing during measurement of the body impedance, suspend the measurement of the body impedance and restart the measurement of the body impedance.

3. The body fat measurement device according to claim 1, wherein the processor is programmed to:
detect an amplitude of the signal waveform expressed by the inputted time-series signal as the amount of change in the measured dimension of the measurement subject's trunk area.

4. The body fat measurement device according to claim 1, wherein the processor is programmed to:
start calculating the trunk area fat mass when the estimated breathing of the measurement subject is in the stopped state.

5. The body fat measurement device according to claim 4, wherein the processor is programmed to:

compare an amplitude of the signal waveform expressed by the inputted time-series signal inputted from the non-contact range sensor during measurement with an amplitude threshold based on an amplitude of a signal waveform expressed by a time-series signal inputted in advance from the non-contact range sensor; and determine whether or not the estimated breathing of the measurement subject is in the stopped state based on a result of the comparison.

6. The body fat measurement device according to claim 5, further comprising:

a memory that stores the time-series signal inputted in advance from the non-contact range sensor, wherein the processor is programmed to:

calculate the amplitude threshold using an amplitude of the signal waveform expressed by the time-series signal in the memory; and compare the amplitude of the signal waveform expressed by the inputted time-series signal inputted from the non-contact range sensor during measurement with the amplitude threshold in the memory; and determine whether or not the estimated breathing of the measurement subject is in the stopped state based on a result of the comparison.

7. The body fat measurement device according to claim 1, wherein the frame member is further provided with the multiple electrodes.

\* \* \* \* \*